US009186128B2

(12) United States Patent
Mugan et al.

(10) Patent No.: US 9,186,128 B2
(45) Date of Patent: Nov. 17, 2015

(54) NEEDLE BIOPSY DEVICE

(75) Inventors: John Mugan, MoyCullen (IE); Brian Murphy, Knocknacarra (IE); John McWeeney, Brighton, MA (US)

(73) Assignee: Covidien LP, Mansfield, MA (US)

( * ) Notice: Subject to any disclaimer, the term of this patent is extended or adjusted under 35 U.S.C. 154(b) by 1040 days.

(21) Appl. No.: 12/243,367

(22) Filed: Oct. 1, 2008

(65) Prior Publication Data

US 2010/0081965 A1 Apr. 1, 2010

(51) Int. Cl.
*A61B 10/00* (2006.01)
*A61B 10/04* (2006.01)
*A61B 10/02* (2006.01)
*A61B 17/00* (2006.01)
*A61B 17/34* (2006.01)
*A61B 19/00* (2006.01)

(52) U.S. Cl.
CPC ............. *A61B 10/04* (2013.01); *A61B 10/0283* (2013.01); *A61B 2017/00424* (2013.01); *A61B 2017/3413* (2013.01); *A61B 2019/4805* (2013.01); *A61B 2019/5425* (2013.01)

(58) Field of Classification Search
CPC ........ A61B 10/00; A61B 10/02; A61B 10/06; A61B 2010/02; A61B 2010/0233; A61B 2010/045; A61B 17/34; A61B 17/3478
USPC ......... 600/407–471, 562, 564, 566, 567–569, 600/571; 604/100, 264, 272; 606/185
See application file for complete search history.

(56) References Cited

U.S. PATENT DOCUMENTS

| | | | | |
|---|---|---|---|---|
| 3,612,050 A | * | 10/1971 | Sheridan | .................. 604/166.01 |
| 3,666,808 A | | 5/1972 | Meek | |
| 4,096,860 A | * | 6/1978 | McLaughlin | ................... 604/44 |
| 4,249,541 A | | 2/1981 | Pratt | |
| 4,655,226 A | | 4/1987 | Lee | |
| 4,838,280 A | | 6/1989 | Haaga | |
| 4,861,341 A | * | 8/1989 | Woodburn | .................... 604/175 |
| 4,903,523 A | | 2/1990 | Flynn | |
| 4,995,866 A | * | 2/1991 | Amplatz et al. | .............. 604/510 |
| 5,054,310 A | | 10/1991 | Flynn | |
| 5,057,085 A | | 10/1991 | Kopans | |
| 5,111,829 A | | 5/1992 | Alvarez de Toledo et al. | |

(Continued)

FOREIGN PATENT DOCUMENTS

EP 0704189 A1 4/1996
EP 0738501 A1 10/1996

(Continued)

OTHER PUBLICATIONS

International Search Report for PCT/US2009/059226 mailed Apr. 28, 2010.

(Continued)

*Primary Examiner* — Rene Towa

(57) ABSTRACT

A device for needle biopsy is provided. The device includes a handle member having proximal and distal portions. A proximal handle member is disposed to the proximal portion of the handle member and a distal handle member is disposed to the distal portion of the handle member. A sheath lumen is disposed within the handle member and extends from the distal portion of the handle member. A needle housing member is partially disposed to the proximal portion of the handle member and a needle is disposed within the sheath lumen. A plurality of protrusions are disposed upon the needle.

9 Claims, 19 Drawing Sheets

(56) References Cited

U.S. PATENT DOCUMENTS

| | | | |
|---|---|---|---|
| 5,257,628 A | 11/1993 | Ishiguro et al. | |
| 5,266,359 A * | 11/1993 | Spielvogel | 427/388.4 |
| 5,277,199 A | 1/1994 | DuBois et al. | |
| 5,320,627 A | 6/1994 | Sorensen et al. | |
| 5,333,613 A | 8/1994 | Tickner et al. | |
| 5,380,292 A | 1/1995 | Wilson | |
| 5,419,310 A | 5/1995 | Frassica et al. | |
| 5,458,112 A | 10/1995 | Weaver | |
| 5,470,308 A | 11/1995 | Edwards et al. | |
| 5,471,988 A | 12/1995 | Fujio et al. | |
| 5,480,389 A * | 1/1996 | McWha et al. | 604/165.02 |
| 5,490,521 A | 2/1996 | Davis et al. | |
| 5,526,822 A | 6/1996 | Burbank et al. | |
| 5,595,724 A | 1/1997 | Deutsch et al. | |
| 5,601,588 A | 2/1997 | Tonomura et al. | |
| 5,607,389 A | 3/1997 | Edwards et al. | |
| 5,609,850 A | 3/1997 | Deutsch et al. | |
| 5,681,348 A | 10/1997 | Sato | |
| 5,688,490 A | 11/1997 | Tournier et al. | |
| 5,695,491 A | 12/1997 | Silverstein | |
| 5,775,333 A | 7/1998 | Burbank et al. | |
| 5,800,445 A | 9/1998 | Ratcliff et al. | |
| 5,810,806 A | 9/1998 | Ritchart et al. | |
| 5,848,978 A | 12/1998 | Cecchi | |
| 5,919,172 A * | 7/1999 | Golba, Jr. | 604/272 |
| 5,921,933 A | 7/1999 | Sarkis et al. | |
| 5,928,164 A | 7/1999 | Burbank et al. | |
| 5,938,635 A * | 8/1999 | Kuhle | 604/506 |
| 5,941,890 A | 8/1999 | Voegele et al. | |
| 5,944,673 A | 8/1999 | Gregoire et al. | |
| 5,947,964 A | 9/1999 | Eggers et al. | |
| 5,967,988 A * | 10/1999 | Briscoe et al. | 600/458 |
| 5,980,469 A | 11/1999 | Burbank et al. | |
| 6,019,733 A | 2/2000 | Farascioni | |
| 6,045,497 A | 4/2000 | Schweich, Jr. et al. | |
| 6,106,473 A | 8/2000 | Violante et al. | |
| 6,106,524 A | 8/2000 | Eggers et al. | |
| 6,117,108 A * | 9/2000 | Woehr et al. | 604/110 |
| 6,133,316 A | 10/2000 | Østensen et al. | |
| 6,149,598 A | 11/2000 | Tanaka | |
| 6,168,779 B1 | 1/2001 | Barsky et al. | |
| 6,171,249 B1 | 1/2001 | Chin et al. | |
| 6,174,291 B1 | 1/2001 | McMahon et al. | |
| 6,179,809 B1 | 1/2001 | Khairkhahan et al. | |
| 6,193,692 B1 | 2/2001 | Harris et al. | |
| 6,221,622 B1 | 4/2001 | Love | |
| 6,228,049 B1 | 5/2001 | Schroeder et al. | |
| 6,231,515 B1 | 5/2001 | Moore et al. | |
| 6,261,302 B1 | 7/2001 | Voegele et al. | |
| 6,273,861 B1 | 8/2001 | Bates et al. | |
| 6,280,399 B1 | 8/2001 | Rossin et al. | |
| 6,287,304 B1 | 9/2001 | Eggers et al. | |
| 6,312,428 B1 | 11/2001 | Eggers et al. | |
| 6,323,335 B1 | 11/2001 | Huang | |
| 6,328,701 B1 | 12/2001 | Terwilliger | |
| 6,333,155 B1 | 12/2001 | Lockhart et al. | |
| 6,334,067 B1 | 12/2001 | Brabrand | |
| 6,336,812 B1 | 1/2002 | Cooper et al. | |
| 6,337,994 B1 | 1/2002 | Stoianovici et al. | |
| 6,338,968 B1 | 1/2002 | Hefti | |
| 6,340,563 B1 | 1/2002 | Finkelstein et al. | |
| 6,340,565 B1 | 1/2002 | Oliner et al. | |
| 6,340,568 B2 | 1/2002 | Hefti | |
| 6,344,316 B1 | 2/2002 | Lockhart et al. | |
| 6,344,317 B2 | 2/2002 | Urnovitz | |
| 6,347,240 B1 | 2/2002 | Foley et al. | |
| 6,347,241 B2 | 2/2002 | Burbank et al. | |
| 6,350,244 B1 | 2/2002 | Fisher | |
| 6,350,274 B1 | 2/2002 | Li | |
| 6,350,583 B1 | 2/2002 | Cohen et al. | |
| 6,351,660 B1 | 2/2002 | Burke et al. | |
| 6,355,033 B1 | 3/2002 | Moorman et al. | |
| 6,355,275 B1 | 3/2002 | Klein | |
| 6,355,424 B1 | 3/2002 | Lorincz et al. | |
| 6,356,782 B1 | 3/2002 | Sirimanne et al. | |
| 6,361,499 B1 | 3/2002 | Bates et al. | |
| 6,361,948 B1 | 3/2002 | Tricoli et al. | |
| 6,364,526 B2 | 4/2002 | Ivan et al. | |
| 6,365,362 B1 | 4/2002 | Terstappen et al. | |
| 6,365,712 B1 | 4/2002 | Kelly | |
| 6,368,280 B1 | 4/2002 | Cermak et al. | |
| 6,368,292 B1 | 4/2002 | Ogden et al. | |
| 6,368,792 B1 | 4/2002 | Billing-Medel et al. | |
| 6,368,795 B1 | 4/2002 | Hefti | |
| 6,368,799 B1 | 4/2002 | Chee | |
| 6,369,195 B1 | 4/2002 | An et al. | |
| 6,371,904 B1 | 4/2002 | Sirimanne et al. | |
| 6,371,917 B1 | 4/2002 | Ferrara et al. | |
| 6,372,431 B1 | 4/2002 | Cunningham et al. | |
| 6,372,444 B1 | 4/2002 | Powers et al. | |
| 6,374,135 B1 | 4/2002 | Bucholz | |
| 6,375,634 B1 | 4/2002 | Carroll | |
| 6,375,953 B1 | 4/2002 | Srivastava et al. | |
| 6,376,258 B2 | 4/2002 | Hefti | |
| 6,379,671 B1 | 4/2002 | Colpitts | |
| 6,379,672 B1 | 4/2002 | Srivastava et al. | |
| 6,383,484 B1 | 5/2002 | Achen et al. | |
| 6,383,491 B1 | 5/2002 | Srivastava et al. | |
| 6,383,492 B1 | 5/2002 | Srivastava et al. | |
| 6,383,493 B1 | 5/2002 | Srivastava et al. | |
| 6,387,056 B1 | 5/2002 | Kieturakis | |
| 6,387,374 B1 | 5/2002 | Srivastava et al. | |
| 6,387,629 B1 | 5/2002 | Schneider et al. | |
| 6,391,306 B1 | 5/2002 | Srivastava et al. | |
| 6,391,542 B1 | 5/2002 | Anderson et al. | |
| 6,391,543 B2 | 5/2002 | Billing-Medel et al. | |
| 6,394,965 B1 | 5/2002 | Klein | |
| 6,395,480 B1 | 5/2002 | Hefti | |
| 6,398,737 B2 | 6/2002 | Moore et al. | |
| 6,399,069 B1 | 6/2002 | Srivastava et al. | |
| 6,399,070 B1 | 6/2002 | Srivastava et al. | |
| 6,399,371 B1 | 6/2002 | Falduto et al. | |
| 6,402,701 B1 | 6/2002 | Kaplan et al. | |
| 6,403,095 B1 | 6/2002 | Srivastava et al. | |
| 6,405,733 B1 | 6/2002 | Fogarty et al. | |
| 6,407,125 B1 | 6/2002 | Fernandez-Pol | |
| 6,409,664 B1 | 6/2002 | Kattan et al. | |
| 6,410,028 B1 | 6/2002 | Srivastava | |
| 6,410,229 B1 | 6/2002 | Lockhart et al. | |
| 6,413,751 B1 | 7/2002 | Benkovic et al. | |
| 6,416,484 B1 | 7/2002 | Miller et al. | |
| 6,421,559 B1 | 7/2002 | Pearlman | |
| 6,423,081 B1 | 7/2002 | Lee et al. | |
| 6,423,313 B1 | 7/2002 | Esmon et al. | |
| 6,423,489 B1 | 7/2002 | Anderson et al. | |
| 6,423,494 B1 | 7/2002 | Jin et al. | |
| 6,423,503 B1 | 7/2002 | Mikolajczyk et al. | |
| 6,426,195 B1 | 7/2002 | Zhong et al. | |
| 6,426,367 B1 | 7/2002 | Das | |
| 6,427,081 B1 | 7/2002 | Burbank et al. | |
| 6,427,089 B1 | 7/2002 | Knowlton | |
| 6,428,463 B1 | 8/2002 | Ravins et al. | |
| 6,428,479 B1 | 8/2002 | Aksnes et al. | |
| 6,428,487 B1 | 8/2002 | Burdorff et al. | |
| 6,432,035 B1 | 8/2002 | Ravins et al. | |
| 6,432,053 B1 | 8/2002 | Fecht et al. | |
| 6,432,065 B1 | 8/2002 | Burdorff et al. | |
| 6,432,700 B1 | 8/2002 | Henderson et al. | |
| 6,434,415 B1 | 8/2002 | Foley et al. | |
| 6,436,054 B1 | 8/2002 | Viola et al. | |
| 6,436,120 B1 | 8/2002 | Meglin | |
| 6,436,394 B1 | 8/2002 | Henderson et al. | |
| 6,436,404 B1 | 8/2002 | Srivastava et al. | |
| 6,436,411 B1 | 8/2002 | Riordan et al. | |
| 6,440,086 B1 | 8/2002 | Hohenberg | |
| 6,440,147 B1 | 8/2002 | Lee et al. | |
| 6,440,151 B1 | 8/2002 | Cragg et al. | |
| 6,440,153 B2 | 8/2002 | Cragg et al. | |
| 6,443,960 B1 | 9/2002 | Brabrand et al. | |
| 6,445,767 B1 | 9/2002 | Karellas | |
| 6,447,477 B2 | 9/2002 | Burney et al. | |
| 6,447,534 B2 | 9/2002 | Cragg et al. | |
| 6,447,780 B1 | 9/2002 | Srivastava et al. | |
| 6,447,781 B1 | 9/2002 | Srivastava | |

(56) References Cited

U.S. PATENT DOCUMENTS

| | | |
|---|---|---|
| 6,447,997 B1 | 9/2002 | Los et al. |
| 6,448,020 B1 | 9/2002 | Toftgard et al. |
| 6,450,973 B1 | 9/2002 | Murphy |
| 6,455,027 B1 | 9/2002 | Barsky et al. |
| 6,455,048 B1 | 9/2002 | Srivastava et al. |
| 6,455,251 B1 | 9/2002 | Waldman |
| 6,459,925 B1 | 10/2002 | Nields et al. |
| 6,461,615 B1 | 10/2002 | Srivastava |
| 6,463,319 B1 | 10/2002 | Bucholz |
| 6,464,648 B1 | 10/2002 | Nakamura |
| 6,465,181 B2 | 10/2002 | Billing-Medel et al. |
| 6,465,183 B2 | 10/2002 | Wolber |
| 6,468,985 B1 | 10/2002 | Huang |
| 6,470,217 B1 | 10/2002 | Fenn et al. |
| 6,471,659 B2 | 10/2002 | Eggers et al. |
| 6,471,700 B1 | 10/2002 | Burbank et al. |
| 6,471,709 B1 | 10/2002 | Fawzi et al. |
| 6,472,518 B1 | 10/2002 | Ribot et al. |
| 6,475,732 B1 | 11/2002 | Shayesteh et al. |
| 6,475,789 B1 | 11/2002 | Cech et al. |
| 6,477,426 B1 | 11/2002 | Fenn et al. |
| 6,482,182 B1 | 11/2002 | Carroll et al. |
| 6,482,599 B1 | 11/2002 | Mikolajczyk et al. |
| 6,485,308 B1 | 11/2002 | Goldstein |
| 6,485,436 B1 | 11/2002 | Truckai et al. |
| 6,485,905 B2 | 11/2002 | Hefti |
| 6,488,636 B2 | 12/2002 | Bryan et al. |
| 6,489,097 B2 | 12/2002 | Hirose et al. |
| 6,489,113 B1 | 12/2002 | Traish |
| 6,490,467 B1 | 12/2002 | Bucholz et al. |
| 6,491,699 B1 | 12/2002 | Henderson et al. |
| 6,491,702 B2 | 12/2002 | Heilbrun et al. |
| 6,492,115 B1 | 12/2002 | Guida et al. |
| 6,494,844 B1 | 12/2002 | Van Bladel et al. |
| 6,494,859 B2 | 12/2002 | Love et al. |
| 6,494,879 B2 | 12/2002 | Lennox et al. |
| 6,495,130 B1 | 12/2002 | Henderson et al. |
| 6,496,717 B2 | 12/2002 | Cox et al. |
| 6,497,706 B1 | 12/2002 | Burbank et al. |
| 6,500,622 B2 | 12/2002 | Bruchez, Jr. et al. |
| 6,500,938 B1 | 12/2002 | Au-Young et al. |
| 6,505,125 B1 | 1/2003 | Ho |
| 6,506,156 B1 | 1/2003 | Jones et al. |
| 6,506,607 B1 | 1/2003 | Shyjan |
| 6,507,748 B2 | 1/2003 | Selland |
| 6,508,755 B1 | 1/2003 | Ravins et al. |
| 6,509,458 B1 | 1/2003 | Afar et al. |
| 6,509,514 B1 | 1/2003 | Kneteman et al. |
| 6,514,248 B1 | 2/2003 | Eggers et al. |
| 6,514,251 B1 | 2/2003 | Ni et al. |
| 6,514,685 B1 | 2/2003 | Moro |
| 6,514,695 B1 | 2/2003 | Barsky et al. |
| 6,517,498 B1 | 2/2003 | Burbank et al. |
| 6,521,211 B1 | 2/2003 | Unger et al. |
| 6,524,800 B2 | 2/2003 | Lockhart et al. |
| 6,527,731 B2 | 3/2003 | Weiss et al. |
| 6,530,888 B2 | 3/2003 | Smith et al. |
| 6,535,756 B1 | 3/2003 | Simon et al. |
| 6,537,761 B1 | 3/2003 | Shayesteh et al. |
| 6,538,119 B2 | 3/2003 | Billing-Medel et al. |
| 6,540,694 B1 | 4/2003 | Van Bladel et al. |
| 6,540,695 B1 | 4/2003 | Burbank et al. |
| 6,544,236 B1 | 4/2003 | Cragg et al. |
| 6,546,787 B1 | 4/2003 | Schiller et al. |
| 6,548,257 B2 | 4/2003 | Lockhart et al. |
| 6,551,255 B2 | 4/2003 | Van Bladel et al. |
| 6,551,784 B2 | 4/2003 | Fodor et al. |
| 6,552,164 B2 | 4/2003 | Colpitts et al. |
| 6,552,181 B1 | 4/2003 | Dean et al. |
| 6,554,779 B2 | 4/2003 | Viola et al. |
| 6,558,407 B1 | 5/2003 | Ivanko et al. |
| 6,558,916 B2 | 5/2003 | Veerapandian et al. |
| 6,562,562 B2 | 5/2003 | Casu' et al. |
| 6,564,087 B1 | 5/2003 | Pitris et al. |
| 6,564,806 B1 | 5/2003 | Fogarty et al. |
| 6,566,078 B1 | 5/2003 | Raitano et al. |
| 6,566,079 B2 | 5/2003 | Hefti |
| 6,567,214 B2 | 5/2003 | Lorincz |
| 6,567,689 B2 | 5/2003 | Burbank et al. |
| 6,568,941 B1 | 5/2003 | Goldstein |
| 6,572,551 B1 | 6/2003 | Smith et al. |
| 6,572,578 B1 | 6/2003 | Blanchard |
| 6,577,904 B1 | 6/2003 | Zhang et al. |
| 6,579,891 B1 | 6/2003 | Fernandez-Pol |
| 6,580,938 B1 | 6/2003 | Acker |
| 6,582,368 B2 | 6/2003 | Holdaway et al. |
| 6,582,426 B2 | 6/2003 | Moorman et al. |
| 6,585,968 B2 | 7/2003 | Little et al. |
| 6,586,713 B2 | 7/2003 | Essenfeld et al. |
| 6,587,578 B2 | 7/2003 | Godik et al. |
| 6,589,240 B2 | 7/2003 | Hinchliffe |
| 6,592,508 B1 | 7/2003 | Ravins et al. |
| 6,592,530 B1 | 7/2003 | Farhadi |
| 6,599,247 B1 | 7/2003 | Stetten |
| 6,602,659 B1 | 8/2003 | Waldman et al. |
| 6,604,404 B2 | 8/2003 | Paltieli et al. |
| 6,605,294 B2 | 8/2003 | Sawhney |
| 6,607,561 B2 | 8/2003 | Brannon |
| 6,608,191 B1 | 8/2003 | Anderson et al. |
| 6,608,310 B2 | 8/2003 | Soluri et al. |
| 6,610,016 B1 | 8/2003 | Violante et al. |
| 6,610,499 B1 | 8/2003 | Fulwyler et al. |
| 6,610,839 B1 | 8/2003 | Morin et al. |
| 6,612,991 B2 | 9/2003 | Sauer et al. |
| 6,613,740 B1 | 9/2003 | Gozes et al. |
| 6,614,921 B1 | 9/2003 | Chung et al. |
| 6,617,110 B1 | 9/2003 | Cech et al. |
| 6,617,137 B2 | 9/2003 | Dean et al. |
| 6,623,437 B2 | 9/2003 | Hinchliffe et al. |
| 6,626,832 B1 | 9/2003 | Paltieli et al. |
| 6,626,848 B2 | 9/2003 | Neuenfeldt |
| 6,626,850 B1 | 9/2003 | Kupec et al. |
| 6,626,903 B2 | 9/2003 | McGuckin, Jr. et al. |
| 6,626,930 B1 | 9/2003 | Allen et al. |
| 6,627,414 B2 | 9/2003 | Billing-Medel et al. |
| 6,627,461 B2 | 9/2003 | Chapman et al. |
| 6,629,959 B2 | 10/2003 | Kuracina et al. |
| 6,631,204 B1 | 10/2003 | Smith |
| 6,632,183 B2 | 10/2003 | Bowman et al. |
| 6,638,234 B2 | 10/2003 | Burbank et al. |
| 6,638,719 B1 | 10/2003 | Gunderson et al. |
| 6,638,727 B1 | 10/2003 | Hung et al. |
| 6,645,731 B2 | 11/2003 | Terstappen et al. |
| 6,647,285 B2 | 11/2003 | Da Silva et al. |
| 6,649,420 B1 | 11/2003 | Cantor |
| 6,652,520 B2 | 11/2003 | Moorman et al. |
| 6,652,859 B1 | 11/2003 | Afar et al. |
| 6,653,080 B2 | 11/2003 | Bruchez et al. |
| 6,653,129 B1 | 11/2003 | Bander et al. |
| 6,654,120 B2 | 11/2003 | Ban |
| 6,659,105 B2 | 12/2003 | Burbank et al. |
| 6,660,834 B2 | 12/2003 | Billing-Medel et al. |
| 6,662,041 B2 | 12/2003 | Burbank et al. |
| 6,663,560 B2 | 12/2003 | MacAulay et al. |
| 6,666,811 B1 | 12/2003 | Good |
| 6,670,122 B2 | 12/2003 | Rosenow et al. |
| 6,673,023 B2 | 1/2004 | Pflueger |
| 6,673,914 B1 | 1/2004 | Hoon |
| 6,675,037 B1 | 1/2004 | Tsekos |
| 6,676,610 B2 | 1/2004 | Morton et al. |
| 6,676,658 B2 | 1/2004 | Burbank et al. |
| 6,676,935 B2 | 1/2004 | Henderson et al. |
| 6,676,984 B1 | 1/2004 | Sharp et al. |
| 6,677,157 B1 | 1/2004 | Cohen |
| 6,678,545 B2 | 1/2004 | Bucholz |
| 6,678,552 B2 | 1/2004 | Pearlman |
| 6,679,851 B2 | 1/2004 | Burbank et al. |
| 6,680,178 B2 | 1/2004 | Harris et al. |
| 6,689,062 B1 | 2/2004 | Mesallum |
| 6,689,065 B2 | 2/2004 | Aksnes et al. |
| 6,689,067 B2 | 2/2004 | Sauer et al. |
| 6,689,071 B2 | 2/2004 | Burbank et al. |
| 6,689,072 B2 | 2/2004 | Kaplan et al. |
| 6,689,073 B2 | 2/2004 | Quay |

(56) References Cited

U.S. PATENT DOCUMENTS

| | | |
|---|---|---|
| 6,689,744 B2 | 2/2004 | Gao et al. |
| 6,689,787 B1 | 2/2004 | McKearn et al. |
| 6,690,371 B1 | 2/2004 | Okerlund et al. |
| 6,690,966 B1 | 2/2004 | Rava et al. |
| 6,690,976 B2 | 2/2004 | Fenn et al. |
| 6,692,467 B2 | 2/2004 | McFarlane |
| 6,692,724 B1 | 2/2004 | Yang et al. |
| 6,692,736 B2 | 2/2004 | Yu et al. |
| 6,695,779 B2 | 2/2004 | Sauer et al. |
| 6,697,665 B1 | 2/2004 | Rava et al. |
| 6,699,205 B2 | 3/2004 | Fulton, III et al. |
| 6,702,749 B2 | 3/2004 | Paladini et al. |
| 6,702,761 B1 | 3/2004 | Damadian et al. |
| 6,702,831 B2 | 3/2004 | Lee et al. |
| 6,703,216 B2 | 3/2004 | Parsons et al. |
| 6,705,994 B2 | 3/2004 | Vortman et al. |
| 6,709,408 B2 | 3/2004 | Fisher |
| 6,709,816 B1 | 3/2004 | Huang et al. |
| 6,712,773 B1 | 3/2004 | Viola |
| 6,712,785 B2 | 3/2004 | Morton et al. |
| 6,714,808 B2 | 3/2004 | Klimberg et al. |
| 6,716,179 B2 | 4/2004 | Burbank et al. |
| 6,722,371 B1 | 4/2004 | Bush et al. |
| 6,723,052 B2 | 4/2004 | Mills |
| 6,723,106 B1 | 4/2004 | Charles et al. |
| 6,723,498 B1 | 4/2004 | Shyjan et al. |
| 6,725,080 B2 | 4/2004 | Melkent et al. |
| 6,725,083 B1 | 4/2004 | Burbank et al. |
| 6,725,095 B2 | 4/2004 | Fenn et al. |
| 6,726,651 B1 | 4/2004 | Robinson et al. |
| 6,728,334 B1 | 4/2004 | Zhao |
| 6,730,042 B2 | 5/2004 | Fulton et al. |
| 6,730,045 B2 | 5/2004 | Finer |
| 6,731,966 B1 | 5/2004 | Spigelman et al. |
| 6,733,969 B2 | 5/2004 | Mack |
| 6,738,663 B2 | 5/2004 | Schroeppel et al. |
| 6,746,844 B2 | 6/2004 | Oliner et al. |
| 6,750,015 B2 | 6/2004 | Horwitz et al. |
| 6,752,154 B2 | 6/2004 | Fogarty et al. |
| 6,752,767 B2 | 6/2004 | Turovskiy et al. |
| 6,752,768 B2 | 6/2004 | Burdorff et al. |
| 6,753,138 B1 | 6/2004 | Schneider et al. |
| 6,758,848 B2 | 7/2004 | Burbank et al. |
| 6,764,449 B2 | 7/2004 | Lee et al. |
| 6,764,495 B2 | 7/2004 | Lee et al. |
| 6,766,186 B1 | 7/2004 | Hoyns et al. |
| 6,767,704 B2 | 7/2004 | Waldman et al. |
| 6,768,925 B2 | 7/2004 | Fenn et al. |
| 6,770,066 B1 | 8/2004 | Leighton et al. |
| 6,770,070 B1 | 8/2004 | Balbierz |
| 6,770,435 B1 | 8/2004 | Billing-Medel et al. |
| 6,770,770 B1 | 8/2004 | Baumann et al. |
| 6,773,903 B2 | 8/2004 | Bova |
| 6,776,757 B2 | 8/2004 | Larson et al. |
| 6,780,984 B2 | 8/2004 | Wang et al. |
| 6,785,410 B2 | 8/2004 | Vining et al. |
| 6,786,870 B2 | 9/2004 | Miyaki et al. |
| 6,788,977 B2 | 9/2004 | Fenn et al. |
| 6,790,185 B1 | 9/2004 | Fisher et al. |
| 6,797,477 B2 | 9/2004 | Guida et al. |
| 6,805,669 B2 | 10/2004 | Swanbom |
| 6,805,869 B2 | 10/2004 | Guo |
| 6,806,712 B2 | 10/2004 | Akgun |
| 6,807,444 B2 | 10/2004 | Tu et al. |
| 6,808,878 B1 | 10/2004 | Gray et al. |
| 6,818,184 B2 | 11/2004 | Fulwyler et al. |
| 6,818,750 B2 | 11/2004 | Reed |
| 6,819,785 B1 | 11/2004 | Vining et al. |
| 6,821,725 B1 | 11/2004 | Carrasco et al. |
| 6,824,780 B1 | 11/2004 | Devaux et al. |
| 6,824,974 B2 | 11/2004 | Pisharody et al. |
| 6,824,995 B1 | 11/2004 | Wu |
| 6,827,692 B2 | 12/2004 | Castellacci |
| 6,831,059 B2 | 12/2004 | Donovan |
| 6,832,111 B2 | 12/2004 | Tu et al. |
| 6,833,373 B1 | 12/2004 | McKearn et al. |
| 6,833,438 B1 | 12/2004 | Afar et al. |
| 6,835,183 B2 | 12/2004 | Lennox et al. |
| 6,835,572 B1 | 12/2004 | Mountford et al. |
| 6,838,243 B2 | 1/2005 | Lai et al. |
| 6,840,952 B2 | 1/2005 | Saker et al. |
| 6,841,350 B2 | 1/2005 | Ogden et al. |
| 6,843,980 B2 | 1/2005 | Green |
| 6,844,153 B2 | 1/2005 | Waldman et al. |
| 6,846,320 B2 | 1/2005 | Ashby et al. |
| 6,846,650 B2 | 1/2005 | Recipon et al. |
| 6,846,911 B2 | 1/2005 | Kelly |
| 6,847,841 B1 | 1/2005 | El Hatw |
| 6,849,080 B2 | 2/2005 | Lee et al. |
| 6,850,588 B2 | 2/2005 | Arenson et al. |
| 6,852,528 B2 | 2/2005 | Yu et al. |
| 6,855,517 B2 | 2/2005 | Salceda et al. |
| 6,855,554 B2 | 2/2005 | Fritsche et al. |
| 6,858,412 B2 | 2/2005 | Willis et al. |
| 6,858,598 B1 | 2/2005 | McKearn et al. |
| 6,858,711 B2 | 2/2005 | McGall et al. |
| 6,859,049 B2 | 2/2005 | Aruntyunyan et al. |
| 6,860,855 B2 | 3/2005 | Shelby et al. |
| 6,860,860 B2 | 3/2005 | Viola |
| 6,863,676 B2 | 3/2005 | Lee et al. |
| 6,864,224 B1 | 3/2005 | Sedivy et al. |
| 6,866,630 B2 | 3/2005 | Larson et al. |
| 6,866,993 B1 | 3/2005 | Williamson |
| 6,866,994 B2 | 3/2005 | Morton |
| 6,867,016 B1 | 3/2005 | Billing-Medel et al. |
| 6,867,753 B2 | 3/2005 | Chinthammit et al. |
| 6,871,086 B2 | 3/2005 | Nevo et al. |
| 6,872,184 B2 | 3/2005 | Brannon |
| 6,872,185 B2 | 3/2005 | Fisher |
| 6,872,389 B1 | 3/2005 | Faris |
| 6,875,182 B2 | 4/2005 | Wardle et al. |
| 6,875,184 B2 | 4/2005 | Morton et al. |
| 6,883,194 B2 | 4/2005 | Corbeil et al. |
| 6,883,958 B2 | 4/2005 | Mayer |
| 6,884,578 B2 | 4/2005 | Warrington et al. |
| 6,884,605 B2 | 4/2005 | Hermonat et al. |
| 6,887,210 B2 | 5/2005 | Quay |
| 6,888,919 B2 | 5/2005 | Graf |
| 6,890,308 B2 | 5/2005 | Islam |
| 6,890,309 B2 | 5/2005 | Fisher |
| 6,890,311 B2 | 5/2005 | Love et al. |
| 6,890,749 B2 | 5/2005 | Billing-Medel et al. |
| 6,893,818 B1 | 5/2005 | Afar et al. |
| 6,893,868 B2 | 5/2005 | Packard et al. |
| 6,894,026 B1 | 5/2005 | Quay |
| 6,899,696 B2 | 5/2005 | Morton et al. |
| 6,900,015 B2 | 5/2005 | Avihingsanon et al. |
| 6,900,049 B2 | 5/2005 | Yu et al. |
| 6,901,278 B1 | 5/2005 | Notelovitz |
| 6,904,305 B2 | 6/2005 | Tsekos |
| 6,904,309 B2 | 6/2005 | Derendorf et al. |
| 6,905,475 B2 | 6/2005 | Hauschild et al. |
| 6,908,440 B2 | 6/2005 | Fisher |
| 6,913,882 B2 | 7/2005 | Glynne et al. |
| 6,914,130 B2 | 7/2005 | Gao et al. |
| 6,916,800 B2 | 7/2005 | McKearn et al. |
| 6,916,918 B2 | 7/2005 | Yu et al. |
| 6,918,881 B2 | 7/2005 | Miller et al. |
| 6,919,176 B2 | 7/2005 | Yang et al. |
| 6,920,347 B2 | 7/2005 | Simon et al. |
| 6,923,809 B2 | 8/2005 | Eggers et al. |
| 6,924,094 B1 | 8/2005 | Gingeras et al. |
| 6,925,389 B2 | 8/2005 | Hitt et al. |
| 6,926,893 B1 | 8/2005 | Hansen |
| 6,927,032 B2 | 8/2005 | Lockhart et al. |
| 6,933,105 B2 | 8/2005 | Jin |
| 6,936,014 B2 | 8/2005 | Vetter et al. |
| 6,936,416 B2 | 8/2005 | Zhu et al. |
| 6,936,687 B1 | 8/2005 | Komoriya et al. |
| 6,942,985 B2 | 9/2005 | Waldman |
| 6,943,236 B2 | 9/2005 | Xu et al. |
| 6,944,505 B2 | 9/2005 | Zhang et al. |
| 6,945,942 B2 | 9/2005 | Van Bladel et al. |
| 6,947,584 B1 | 9/2005 | Avila et al. |

(56) References Cited

U.S. PATENT DOCUMENTS

| | | |
|---|---|---|
| 6,949,357 B2 | 9/2005 | Billing-Medel et al. |
| 6,953,691 B2 | 10/2005 | Reed et al. |
| 6,954,667 B2 | 10/2005 | Treado et al. |
| 6,955,653 B2 | 10/2005 | Eggers |
| 6,965,793 B2 | 11/2005 | Treado et al. |
| 6,994,712 B1 | 2/2006 | Fisher et al. |
| D518,175 S | 3/2006 | Hardin, Jr. et al. |
| 7,014,610 B2 | 3/2006 | Koulik |
| 7,025,765 B2 | 4/2006 | Balbierz et al. |
| 7,067,111 B1 | 6/2006 | Yang et al. |
| 7,067,274 B2 | 6/2006 | Fairbrother et al. |
| 7,070,816 B2 | 7/2006 | Newmark et al. |
| 7,072,704 B2 | 7/2006 | Bucholz |
| 7,074,600 B2 | 7/2006 | Dean et al. |
| 7,077,842 B1 | 7/2006 | Cosman |
| 7,079,132 B2 | 7/2006 | Sauer et al. |
| 7,081,340 B2 | 7/2006 | Baker et al. |
| 7,083,547 B2 | 8/2006 | LaStayo et al. |
| 7,083,985 B2 | 8/2006 | Hefti et al. |
| 7,087,393 B2 | 8/2006 | Billing-Medel et al. |
| 7,089,121 B1 | 8/2006 | Wang |
| 7,090,845 B2 | 8/2006 | Fong et al. |
| 7,090,862 B2 | 8/2006 | Barrett-Reis et al. |
| 7,091,047 B2 | 8/2006 | Serrero |
| 7,094,233 B2 | 8/2006 | Desinger |
| 7,101,663 B2 | 9/2006 | Godfrey et al. |
| 7,101,862 B2 | 9/2006 | Cochrum et al. |
| 7,108,969 B1 | 9/2006 | Warrington et al. |
| 7,115,368 B2 | 10/2006 | Powers et al. |
| 7,118,876 B2 | 10/2006 | Tyner et al. |
| 7,118,910 B2 | 10/2006 | Unger et al. |
| 7,122,011 B2 | 10/2006 | Clifford et al. |
| 7,122,653 B2 | 10/2006 | Cohen et al. |
| 7,125,836 B2 | 10/2006 | Woodward |
| 7,125,969 B1 | 10/2006 | Benz et al. |
| 7,128,877 B2 | 10/2006 | Quay et al. |
| 7,128,893 B2 | 10/2006 | Leamon et al. |
| 7,129,048 B2 | 10/2006 | Bruchez et al. |
| 7,131,951 B2 | 11/2006 | Angel |
| 7,135,333 B1 | 11/2006 | Waldman et al. |
| 7,139,601 B2 | 11/2006 | Bucholz et al. |
| 7,141,019 B2 | 11/2006 | Pearlman |
| 7,144,950 B2 | 12/2006 | Bazan et al. |
| 7,153,700 B1 | 12/2006 | Pardee et al. |
| 7,156,814 B1 | 1/2007 | Williamson, IV et al. |
| 7,156,815 B2 | 1/2007 | Leigh et al. |
| 7,160,292 B2 | 1/2007 | Moorman et al. |
| 7,161,057 B2 | 1/2007 | Kneteman et al. |
| 7,169,114 B2 | 1/2007 | Krause |
| 7,172,558 B2 | 2/2007 | Olson, Jr. |
| 7,172,739 B2 | 2/2007 | Maughan |
| 7,175,839 B1 | 2/2007 | Hiserodt |
| 7,183,251 B1 | 2/2007 | Russo et al. |
| D538,933 S | 3/2007 | Andrade |
| 7,186,522 B2 | 3/2007 | Lapen et al. |
| 7,189,206 B2 | 3/2007 | Quick et al. |
| 7,189,207 B2 | 3/2007 | Viola |
| 7,190,378 B2 | 3/2007 | Sauer et al. |
| 7,192,570 B2 | 3/2007 | Maecke et al. |
| 7,195,774 B2 | 3/2007 | Carvalho et al. |
| 7,195,868 B2 | 3/2007 | Iartchouk et al. |
| 7,195,911 B2 | 3/2007 | Cech et al. |
| 7,196,182 B2 | 3/2007 | Reed et al. |
| 7,198,896 B2 | 4/2007 | Rush et al. |
| 7,199,234 B2 | 4/2007 | Morin et al. |
| 7,204,988 B2 | 4/2007 | Cheung |
| 7,207,985 B2 | 4/2007 | Duong et al. |
| 7,208,146 B2 | 4/2007 | Denney, Jr. |
| 7,208,267 B2 | 4/2007 | Salceda et al. |
| 7,211,398 B2 | 5/2007 | Astle et al. |
| 7,214,489 B2 | 5/2007 | Bazan et al. |
| 7,217,276 B2 | 5/2007 | Henderson et al. |
| 7,217,394 B2 | 5/2007 | Studer |
| 7,218,959 B2 | 5/2007 | Alfano et al. |
| 7,220,258 B2 | 5/2007 | Myhr |
| 7,220,891 B2 | 5/2007 | Barsky et al. |
| 7,223,238 B2 | 5/2007 | Swanbom |
| 7,223,380 B2 | 5/2007 | Yang et al. |
| 7,223,540 B2 | 5/2007 | Pourmand et al. |
| 7,223,542 B2 | 5/2007 | Raitano et al. |
| 7,226,731 B1 | 6/2007 | Chuaqui et al. |
| 7,227,009 B2 | 6/2007 | Craik et al. |
| 7,229,413 B2 | 6/2007 | Violante et al. |
| 7,229,417 B2 | 6/2007 | Foerster et al. |
| 7,229,439 B2 | 6/2007 | Burbank et al. |
| 7,229,604 B2 | 6/2007 | Yang et al. |
| 7,229,774 B2 | 6/2007 | Chinnaiyan et al. |
| 7,231,015 B2 | 6/2007 | Kumakhov |
| 7,235,047 B2 | 6/2007 | MacAulay et al. |
| 7,236,816 B2 | 6/2007 | Kumar et al. |
| 7,241,736 B2 | 7/2007 | Hunter et al. |
| 7,244,619 B2 | 7/2007 | Contreras et al. |
| 7,245,748 B2 | 7/2007 | Degani et al. |
| 7,245,958 B1 | 7/2007 | Navab et al. |
| 7,247,426 B2 | 7/2007 | Yakhini et al. |
| 7,250,180 B2 | 7/2007 | Arellano |
| 7,250,264 B2 | 7/2007 | Fong et al. |
| 7,250,551 B2 | 7/2007 | Tsai et al. |
| 7,251,352 B2 | 7/2007 | Sauer et al. |
| 7,251,568 B2 | 7/2007 | Pittman et al. |
| 7,252,935 B2 | 8/2007 | Sidransky |
| 7,252,946 B2 | 8/2007 | Szasz |
| 7,252,948 B2 | 8/2007 | Gingeras et al. |
| 7,258,973 B2 | 8/2007 | Astle et al. |
| 7,261,712 B2 | 8/2007 | Burbank et al. |
| 7,261,875 B2 | 8/2007 | Li et al. |
| 7,262,288 B1 | 8/2007 | Cech et al. |
| 7,264,947 B2 | 9/2007 | Gozes et al. |
| 7,270,956 B2 | 9/2007 | Bazan et al. |
| 7,271,187 B2 | 9/2007 | Neuberger et al. |
| 7,274,810 B2 | 9/2007 | Reeves et al. |
| 2001/0007925 A1 | 7/2001 | Ritchart et al. |
| 2001/0023322 A1 | 9/2001 | Espositio et al. |
| 2001/0047183 A1 | 11/2001 | Privitera et al. |
| 2002/0035324 A1 | 3/2002 | Sirimanne et al. |
| 2002/0082519 A1 | 6/2002 | Miller et al. |
| 2002/0156395 A1 | 10/2002 | Stephens et al. |
| 2002/0169418 A1* | 11/2002 | Menzi et al. ............ 604/164.07 |
| 2003/0078502 A1 | 4/2003 | Miyaki et al. |
| 2003/0093007 A1 | 5/2003 | Wood |
| 2003/0105488 A1 | 6/2003 | Chu |
| 2003/0163142 A1 | 8/2003 | Paltieli et al. |
| 2003/0181823 A1 | 9/2003 | Gatto |
| 2003/0195436 A1 | 10/2003 | Van Bladel et al. |
| 2003/0204137 A1 | 10/2003 | Chesbrough et al. |
| 2003/0208134 A1 | 11/2003 | Secrest et al. |
| 2003/0212394 A1 | 11/2003 | Pearson et al. |
| 2003/0233101 A1 | 12/2003 | Lubock et al. |
| 2004/0073219 A1 | 4/2004 | Skiba et al. |
| 2004/0077948 A1 | 4/2004 | Violante et al. |
| 2004/0153005 A1 | 8/2004 | Krueger |
| 2004/0167429 A1 | 8/2004 | Roshdieh et al. |
| 2004/0167432 A1 | 8/2004 | Burbank et al. |
| 2004/0236212 A1 | 11/2004 | Jones et al. |
| 2004/0260199 A1* | 12/2004 | Hardia et al. ................ 600/566 |
| 2005/0021003 A1 | 1/2005 | Caso et al. |
| 2005/0022493 A1 | 2/2005 | Olinger et al. |
| 2005/0061697 A1 | 3/2005 | Moberg |
| 2005/0113715 A1 | 5/2005 | Schwindt et al. |
| 2005/0143753 A1 | 6/2005 | Whitmore et al. |
| 2005/0159676 A1 | 7/2005 | Taylor et al. |
| 2005/0192535 A1* | 9/2005 | Takagi et al. ............ 604/164.08 |
| 2005/0228311 A1 | 10/2005 | Beckman et al. |
| 2005/0228312 A1* | 10/2005 | Surti ............................ 600/567 |
| 2005/0228413 A1 | 10/2005 | Binmoeller et al. |
| 2005/0251111 A1 | 11/2005 | Saito et al. |
| 2005/0256426 A1 | 11/2005 | Brugge |
| 2006/0052750 A1 | 3/2006 | Lenker et al. |
| 2006/0100654 A1* | 5/2006 | Fukuda et al. ................ 606/181 |
| 2006/0116605 A1 | 6/2006 | Nakao |
| 2006/0142789 A1* | 6/2006 | Lehman et al. ............ 606/153 |
| 2006/0155210 A1 | 7/2006 | Beckman et al. |
| 2006/0167416 A1 | 7/2006 | Mathis et al. |
| 2006/0189891 A1 | 8/2006 | Waxman et al. |

(56) References Cited

U.S. PATENT DOCUMENTS

| | | |
|---|---|---|
| 2006/0235298 A1 | 10/2006 | Kotmel et al. |
| 2006/0247530 A1 | 11/2006 | Hardin et al. |
| 2006/0258955 A1 | 11/2006 | Hoffman et al. |
| 2007/0023304 A1 | 2/2007 | Joyce et al. |
| 2007/0032741 A1 | 2/2007 | Hibner et al. |
| 2007/0038089 A1 | 2/2007 | Hatano et al. |
| 2007/0055173 A1 | 3/2007 | DeLonzor et al. |
| 2007/0060837 A1* | 3/2007 | Cho et al. ............ 600/562 |
| 2007/0118049 A1 | 5/2007 | Viola |
| 2007/0123799 A1 | 5/2007 | Meireles |
| 2007/0123800 A1 | 5/2007 | Nishtala et al. |
| 2007/0149893 A1 | 6/2007 | Heske et al. |
| 2007/0177009 A1 | 8/2007 | Bayer et al. |
| 2007/0185411 A1 | 8/2007 | Hibner |
| 2007/0213633 A1 | 9/2007 | McClellan |
| 2007/0213634 A1 | 9/2007 | Teague |
| 2007/0299306 A1 | 12/2007 | Parasher et al. |
| 2008/0058637 A1 | 3/2008 | Fischell et al. |
| 2008/0097344 A1 | 4/2008 | McKinnon et al. |
| 2008/0097572 A1 | 4/2008 | Sheldon et al. |
| 2008/0146962 A1 | 6/2008 | Ritchie et al. |
| 2008/0147010 A1 | 6/2008 | Nakajima et al. |
| 2008/0200912 A1 | 8/2008 | Long |
| 2008/0300462 A1 | 12/2008 | Intoccia et al. |
| 2008/0319341 A1 | 12/2008 | Taylor et al. |
| 2009/0054773 A1* | 2/2009 | Shizuka ............ 600/439 |
| 2009/0069679 A1 | 3/2009 | Hibi |
| 2009/0099414 A1 | 4/2009 | Goto et al. |
| 2009/0177114 A1* | 7/2009 | Chin et al. ............ 600/565 |
| 2009/0182200 A1 | 7/2009 | Golden et al. |
| 2010/0081965 A1 | 4/2010 | Mugan et al. |
| 2010/0121218 A1 | 5/2010 | Mugan et al. |
| 2010/0274085 A1 | 10/2010 | Mugan et al. |
| 2012/0116248 A1 | 5/2012 | Mcweeney et al. |

FOREIGN PATENT DOCUMENTS

| | | |
|---|---|---|
| EP | 1870051 A1 | 12/2007 |
| EP | 2030574 A2 | 3/2009 |
| EP | 09818508 | 4/2010 |
| EP | 09829751 | 6/2010 |
| JP | 6-189965 A | 7/1994 |
| JP | 7-116169 A | 5/1995 |
| JP | 8-38482 A | 2/1996 |
| JP | 9-135836 A | 5/1997 |
| JP | 2007-513692 A | 5/2007 |
| WO | WO-8605324 A1 | 12/1986 |
| WO | WO-9200039 A1 | 1/1992 |
| WO | 92/04062 A1 | 3/1992 |
| WO | WO-0009178 A1 | 2/2000 |
| WO | 00/33909 A1 | 6/2000 |
| WO | WO-0046626 A1 | 10/2000 |
| WO | WO-2004066828 A2 | 8/2004 |
| WO | WO-2004066829 A2 | 8/2004 |
| WO | WO-2004073509 A1 | 9/2004 |
| WO | WO-2005020905 A2 | 3/2005 |
| WO | WO-2005081032 A1 | 9/2005 |
| WO | WO-2005081033 A1 | 9/2005 |
| WO | 2005/096953 A2 | 10/2005 |
| WO | 2005/096963 A2 | 10/2005 |
| WO | WO-2005112797 A1 | 12/2005 |
| WO | WO-2005120345 A2 | 12/2005 |
| WO | WO-2006014011 A1 | 2/2006 |
| WO | WO-2006028281 A1 | 3/2006 |
| WO | WO-2006057443 A1 | 6/2006 |
| WO | WO-2006064972 A1 | 6/2006 |
| WO | WO-2007021904 A2 | 2/2007 |
| WO | WO-2007021904 A3 | 2/2007 |
| WO | WO-2007081039 A2 | 7/2007 |
| WO | WO-2007081041 A1 | 7/2007 |
| WO | WO-2007081050 A1 | 7/2007 |
| WO | WO-2007081056 A1 | 7/2007 |
| WO | WO-2008020157 A1 | 2/2008 |
| WO | WO-2008020439 A2 | 2/2008 |
| WO | WO-2008024684 A2 | 2/2008 |
| WO | WO-2008044013 A2 | 4/2008 |
| WO | 2012/112202 A1 | 8/2012 |
| WO | 2013/074653 A1 | 5/2013 |

OTHER PUBLICATIONS

International Search Report for PCT/US2008/088431 mailed Jul. 27, 2009.
International Search Report for PCT/US2009/065705 mailed Jul. 7, 2010.
International Search Report and Written Opinion mailed Jul. 7, 2010 as issued in PCT/US2009/065705, 13 pages.
International Search Report and Written Opinion dated May 2, 2013 issued in PCT/US2012/065049, 17 pages.
Iglesias-Garcia, 2011, Feasibility and yield of a new EUS histology needle: results from a multicenter, pooled, cohort study, Gastrointestinal Endoscopy 73(6); 1189-1196.
International Search Report for PCT/US2004/040221 maled Jun. 13, 2005.
International Search Report for PCT/US2012/065049 mailed Feb. 22, 2013.
Iwashita, 2013, High single-pass diagnostic yield of a new 25-gauge core biopsy needle for EUS-guided FNA biopsy in solid pancreatic lesions, Gastrointestinal Endoscopy 77(6); 909-915.
Kahaleh, 2013, Endoscopic ultrasonography guided biliary drainage: Summary of consortium meeting, May 7, 2011 Chicago, World Journal of Gastroenterology, 19(9); 1372-1379.
Khashab, 2013, EUS-guided biliary drainage by using a standardized approach for malignant biliary obstruction: rendezvous versus direct transluminal techniques, Gastrointestinal Endoscopy; 1-8.
Park, 2011, EUS-guided biliary drainage with transluminal stenting after failed ERCP: predictors of adverse events and long-term results, Gastrointestinal Endoscopy 74(6); 1276-1284.
Park, 2013, Prospective evaluation of a treatment algorithm with enhanced guidewire manipulation protocol for EUS-guided biliary drainage after failed ERCP, Gastrointestinal Endoscopy 78(1); 92-101.
Pelaez-Luna, 2008, Interventional EUS guided cholangiography. First description in Mexico of a novel, secure and feasible technique. A case report, Caso clinico.
International Search Report for PCT/JP2007/053498 mailed Mar. 20, 2007.
Creganna Needle Brochure dated Jan. 16, 2008.
International Search Report and Written Opinion issued in PCT/US2011/060981, having a mailing date of Jun. 11, 2012.
International Search Report and Written Opinion issued in PCT/JP2007/053498, having a mailing date of Mar. 20, 2007.

* cited by examiner

NEEDLE BIOPSY DEVICE

BACKGROUND

1. Technical Field

The present disclosure generally relates to the biopsy devices, and more particularly, needle biopsy devices for collecting tissue, fluid, and cell samples in conjunction with procedures such as endoscopic ultrasound or endoscopic bronchial ultrasound.

2. Background of the Invention

Endoscopic ultrasounds have been used for more than twenty five years within the field of medicine. These procedures allow clinicians to scan, locate and identify individual layers of the gastrointestinal (GI) tract and determine the location of individual mucosal and submucosal layers. As a result, appropriate therapeutic modes of treatment for malignancies and various abnormalities may be determined.

An endoscopic ultrasound procedure consist of several steps. First, a clinician sedates a patient and inserts a probe via esophagogastroduodenoscopy into the patient's stomach and duodenum. Second, an endoscope is passed through the patient's mouth and advanced to the level of the duodenum. Third, from various positions between the esophagus and duodenum, organs or masses outside the gastrointestinal tract are imaged to determine abnormalities. Fourth, organs or masses can be biopsed through the process of "fine needle aspiration" (FNA) if any abnormalities are present.

Endoscopic ultrasounds and endoscopic bronchial ultrasounds through fine needle aspiration are presently the standard modes of treatment in the field of gastrointestinal endoscopy and bronchoscopy. These procedures traditionally result in high yields of sensitivity and specificity in the management of indications of diseases such as esophageal cancer, pancreatic cancer, liver mass, non-small cell lung cancer, pancreatic mass, endobronchial mass, and intra-abdominal lymph nodes.

An endoscopic ultrasound through fine needle aspiration requires a device that is attached to the luer port or working channel of a typical echoendoscope. Prior art devices utilize a series of push and pull handles to control the axial movement of the catheter shaft of the device and the depth of needle penetration. These devices, however, suffer from several drawbacks.

First, the means of attaching a device to an echoendoscope is cumbersome. For example, these devices presently utilize male fitting adapters that must be screwed onto a female luer port of an endoscope. Second, prior art devices provide suboptimal ergonomics of use. More specifically, a clinician must actuate a number of handles independently and lock respective handles in position via cap screw arrangement to secure the device. The cumulative actions required by a clinician result in significantly drawn out procedures. Third, needles commonly kink or deform during removal from a device causing numerous delays and failures. Fourth, multiple passes per procedure are required, which prolong the procedure and result in a clinician needing to reconfirm the location of a needle relative to a desired aspiration site with each new pass.

Additionally, prior art devices are not designed to individually accommodate needles of various diameters. Specifically, a device must be removed from an endoscope during a procedure if a clinician chooses to utilize multiple needle sizes. For example, a clinician may begin an endoscopic ultrasound procedure with: 1) a device having a needle with a diameter of 19 AWG; 2) aspirate; 3) remove the needle housing member from the device; 4) remove the device from the endoscope; 5) attach a new device to the endoscope and insert a needle having a diameter of 22 AWG; and 6) track the needle through the device's sheath lumen and continue the procedure. In this instance, absent removing the device from an endoscope, the difference in the clearance between the inner diameter of the sheath and the outer diameter of the needle will increase when moving from a large needle to a smaller needle. As a result, instability in the ability of the needle to puncture a desired lesion or cyst can result causing increased manipulation time for the clinician and loss of procedural efficiency.

Therefore, a need exists for an improved device for use in endoscopic ultrasound procedures.

SUMMARY

Accordingly, a device for needle biopsy is provided for collecting tissue, fluid, and cell samples in conjunction with procedures such as an endoscopic ultrasound or endoscopic bronchial ultrasound.

In a first aspect, a device for needle biopsy comprises a handle member having proximal and distal portions, a proximal handle member disposed to the proximal portion of the handle member, and a distal handle member disposed to the distal portion of the handle member. A sheath lumen is disposed within the handle member and extends from the distal portion of the handle member. Additionally, a needle housing member is partially disposed to the proximal portion of the handle member. A needle is also disposed within the sheath lumen and a plurality of protrusions are disposed thereon.

In one embodiment, a plurality of protrusions can be distributed along the length of the needle. Alternatively, the plurality of protrusions may be located at a consistent increment over the length of the needle. Additionally, the protrusions can be distributed on at least a portion of the length of the needle.

In another embodiment, at least a portion of the needle can include a tapered region for increasing the overall dimension of the needle. The tapered region and the sheath lumen may provide interference for creating stability for the needle as it passes through the sheath lumen. The interference can be a drag force creating frictional resistance between an outer diameter of the needle and an inner diameter of the sheath lumen. In another embodiment, at least a portion of the needle may also include materials or design features to enhance echogenicity and ultrasonic visibility. In a further embodiment, a stylet is disposed within the needle.

In a second aspect, a device for needle biopsy comprises a handle member having proximal and distal portions, a proximal handle member disposed to the proximal portion of the handle member, and a distal handle member disposed to the distal portion of the handle member. A sheath lumen is disposed within the handle member and extends from the distal portion of the handle member. Additionally, a needle housing member is partially disposed to the proximal portion of the handle member. Furthermore, a needle is disposed within the sheath lumen and at least a portion of the needle is surrounded by a polymer.

In one embodiment, a polymer may be comprised of lubricous materials. The polymer may also increase the overall dimension of the needle to create stability for the needle as it passes through the sheath lumen. In another embodiment, at least a portion of the needle may also include materials or design features to enhance echogenicity and ultrasonic visibility. In a further embodiment, a stylet is disposed within the needle.

In a third aspect, a device for needle biopsy comprises a handle member having proximal, distal, and stop portions, a proximal handle member disposed to the proximal portion of the handle member, and a distal handle member disposed to the distal portion of the handle member. The proximal handle member is configured for slideable engagement to the proximal portion of the handle member and includes a friction member. The friction member engages at least one indentation of a first series of indentations along the proximal portion of the handle member to limit slideable movement. The distal handle member is configured for slideable engagement to the distal portion of the handle member and includes friction members. The friction members engages at least one indentation of a second series of indentations along the distal portion of the handle member to limit slideable movement. A sheath lumen is disposed within the handle member and extends from the distal portion of the handle member. A needle housing member is partially disposed to the proximal portion of the handle member and includes a needle that is disposed within the sheath lumen.

In one embodiment, at least one indentation of the first series of indentations may represent the length by which the needle extends beyond a distal portion of the sheath member. Additionally, at least one indentation of the second series of indentations may represent the length by which the sheath member extends beyond the distal portion of the distal handle member.

In another embodiment, a stop portion of the handle member is disposed between the proximal and distal handle members. The stop portion can prevent axial movement of the proximal handle member into the distal handle member and axial movement of the distal handle member into the proximal handle member.

In another embodiment, friction members may include a male indentation having a mating end configured to engage to a female indentation. The friction member may also include a female indentation having a mating end configured to engage to a male indentation. In another embodiment, at least a portion of the needle may also include materials or design features to enhance echogenicity and ultrasonic visibility. In a further embodiment, a stylet is disposed within the needle.

In a fourth aspect, a device for needle biopsy comprises a handle member having proximal and distal portions, a proximal handle member disposed to the proximal portion of the handle member, and a distal handle member disposed to the distal portion of the handle member. The distal handle member includes a connector having a release member that connects axially to a medical device and engages and disengages to a channel port of the medical device. Additionally, a sheath lumen is disposed within the handle member and extends from the distal portion of the handle member. Furthermore, a needle housing member is partially disposed to the proximal portion of the handle member and includes a needle that is disposed within the sheath lumen.

In one embodiment, a channel port may be a luer port of the medical device. In another embodiment, a connector may include at least two adaptations to connect to the medical device. The two adaptations may also connect relative to the longitudinal axis of the medical device. In another embodiment, the connector is disposed to the distal portion of the distal handle member. The release member may also be depressible. In another embodiment, at least a portion of the needle may also include materials or design features to enhance echogenicity and ultrasonic visibility. In a further embodiment, a stylet is disposed within the needle.

In a fifth aspect, a device for needle biopsy comprises a handle member having proximal and distal portions, a proximal handle member disposed to the proximal portion of the handle member, and a distal handle member disposed to the distal portion of the handle member. The proximal handle member includes at least one adaptation member. A sheath lumen is disposed within the handle member and extends from the distal portion of the handle member. A needle housing member is partially disposed to the proximal portion of the handle member that is moveable in a substantially transverse direction relative to the longitudinal axis of the handle member. The needle housing member includes a needle that is disposed within the sheath lumen and a strain relief member.

In one embodiment, a needle housing member may include at least one indentation for engaging to at least one adaptation member. In another embodiment, a needle housing member can detach from the proximal handle member by moving the needle housing member in the substantially transverse direction. This movement can cause at least one indentation to disengage from at least one adaptation member.

In another embodiment, the proximal handle member can include a release member that engages and disengages the needle housing member. Additionally, the release member may also be depressible. In other embodiments, the strain relief member may provide a semi-flexible transition between at least one adaptation member and the needle to reduce deformation of the needle during removal from the proximal handle member. In another embodiment, at least a portion of the needle may also include materials or design features to enhance echogenicity and ultrasonic visibility. In a further embodiment, a stylet is disposed within the needle.

In a sixth aspect, a device for needle biopsy comprises a handle member having proximal and distal portions, a proximal handle member disposed to the proximal portion of the handle member, and a distal handle member disposed to the distal portion of the handle member. A sheath lumen is disposed within the handle member and extends from the distal portion of the handle member. A needle housing member is partially disposed to the proximal portion of the handle member that is moveable in a substantially transverse direction relative to the longitudinal axis of the handle member. A needle having a plurality of protrusions disposed thereon is disposed within the sheath lumen.

In one embodiment, a plurality of protrusions may be distributed along the length of the needle. The plurality of protrusions may also be located at a consistent increment over the length of the needle. Additionally, the protrusions may be distributed on at least a portion of the length of the needle.

In another embodiment, at least a portion of the needle can include a tapered region for increasing the overall dimension of the needle. The tapered region and the sheath lumen can provide interference for creating stability for the needle as it passes through the sheath lumen. This interference may be a drag force creating frictional resistance between an outer diameter of the needle and an inner diameter of the sheath lumen.

In another embodiment, a needle housing member can include at least one indentation for engaging to at least one adaptation member. The needle housing member can detach from the proximal handle member by moving the needle housing member in a substantially transverse direction, thereby causing at least one indentation to disengage from at least one adaptation. The proximal handle member may also include a release member that engages and disengages the needle housing member. Additionally, the release member may be depressible. In another embodiment, a strain relief member reduces a drag force between the needle and sheath lumen as the needle is removed from the sheath lumen. In other embodiments, at least a portion of the needle may also include materials or design features to enhance echogenicity and ultrasonic visibility. In a further embodiment, a stylet is disposed within the needle.

In a seventh aspect, a device for needle biopsy comprises a handle member having proximal and distal portions, a proximal handle member disposed to the proximal portion of the handle member, and a distal handle member disposed to the distal portion of the handle member. The proximal handle member is configured for slideable engagement to the proximal portion of the handle member and includes a friction member. The friction member engages at least one indentation of a first series of indentations along the proximal portion of the handle member to limit slideable movement. The distal handle member is configured for slideable engagement to the distal portion of the handle member and includes a friction member. The friction member engages at least one indentation of a second series of indentations along the distal portion of the handle member to limit slideable movement. A sheath lumen is disposed within the handle member and extends from the distal portion of the handle member. A needle housing member is partially disposed to the proximal portion of the handle member. A needle including a plurality of protrusions disposed thereon is disposed within the sheath lumen. At least a portion of the needle is surrounded by a polymer.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings as set forth below:

DETAILED DESCRIPTION OF EXEMPLARY EMBODIMENTS

The exemplary embodiments of the needle biopsy device and methods of operation disclosed are discussed in terms of needle biopsy devices for collecting tissue, fluid, and cell samples from a body in conjunction with an endoscopic ultrasound or endoscopic bronchial ultrasound. It is envisioned that the present disclosure, however, finds application to a wide variety of biopsy devices for the collection of samples from a subject. It is also envisioned that the present disclosure may be employed for collection of body fluids including those employed during procedures relating to phlebotomy, digestive, intestinal, urinary, veterinary, etc. It is contemplated that the needle biopsy device may be utilized with other needle biopsy applications including, but not limited to, fluid collection, catheters, catheter introducers, spinal and epidural biopsy, aphaeresis, dialysis, etc.

In the discussion that follows, the term "proximal" refers to a portion of a structure that is closer to a clinician, and the term "distal" refers to a portion that is further from the clinician. According to the present disclosure, the term "clinician" refers to an individual performing sample collection, installing or removing a needle from a needle biopsy device, and may include support personnel. Reference will now be made in detail to exemplary embodiments of the disclosure, which are illustrated in the accompanying figures.

Figure 1:
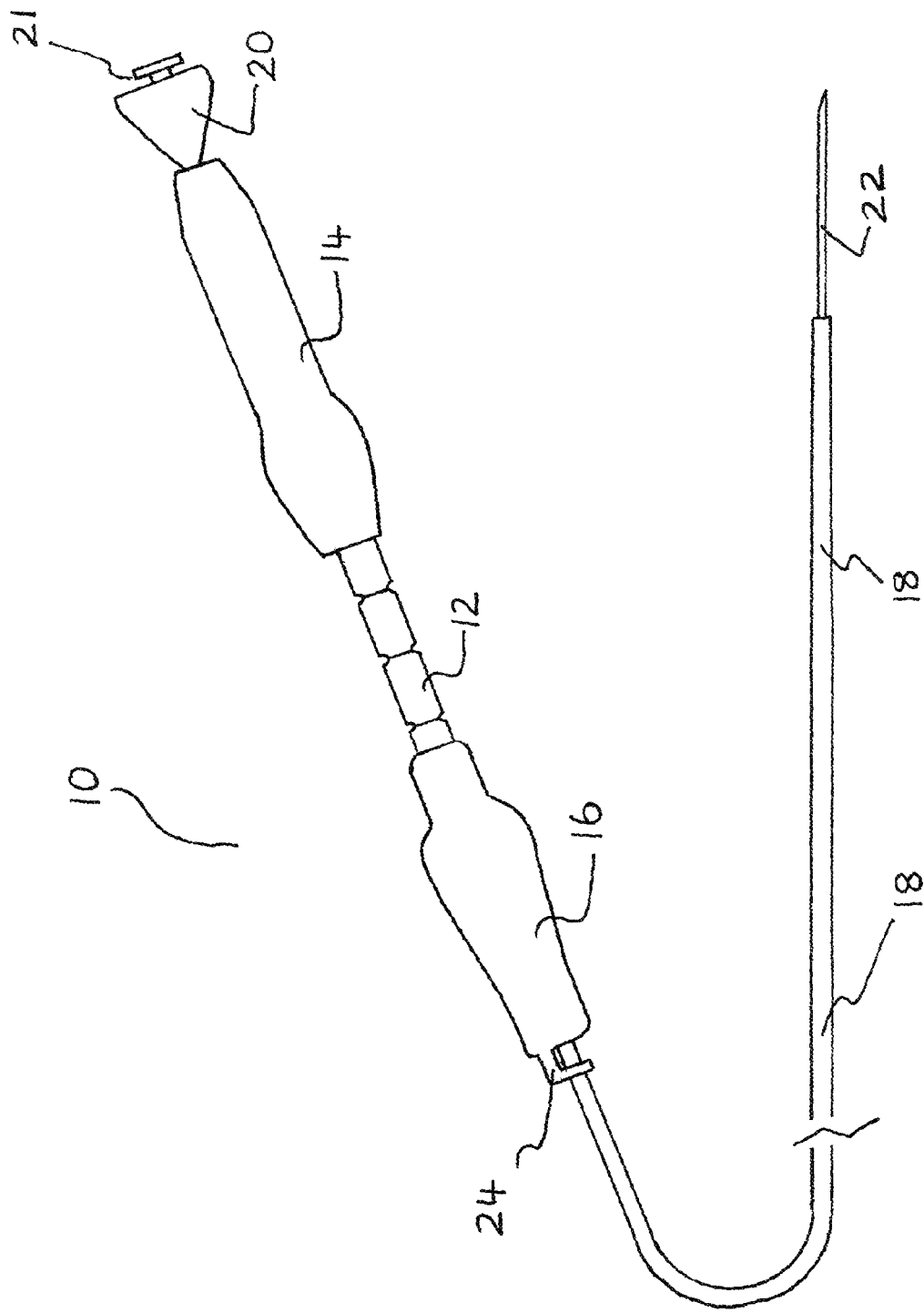
FIG. 1 is a perspective view of a needle biopsy device.

Referring to FIG. 1, a needle biopsy device 10 is provided for fine needle aspiration during procedures such as endoscopic ultrasound. The device 10 is generally comprised of a handle 12, a proximal handle member 14, a distal handle member 16, a sheath lumen 18, a needle housing member 20, a stylet 21, a needle 22, and a connector 24.

In one embodiment, a clinician connects the device 10 to another medical device via the connector 24. The clinician subsequently inserts the needle housing member 20, which includes the stylet 21 and the needle 22, into the proximal portion of the proximal handle member 14. The stylet 21 may be, but is not limited to, a removable coaxial thin wire which is passed within the lumen of the needle 22. It is envisioned that the stylet 21 may provide rigidity and stability to the needle 22. Additionally, it is contemplated that the stylet 21 can protect the needle 22 from damage or inadvertent collection of samples.

Upon passing the needle 22 through the sheath lumen 18, the clinician may slideably manipulate the proximal handle member 14 and the distal handle member 16 along the axis of the handle 12. At this juncture, the clinician may lock the proximal handle member 14 and the distal handle member 16 at various depths along the handle 12. Movement of the proximal handle member 14 causes the needle 22 to extend from the distal portion of the sheath 18. Additionally, movement of the distal handle member 16 adjusts the depth of exposure of the sheath 18. A clinician may subsequently withdraw the stylet 21 from the needle housing member 20 and begin needle aspiration.

Figure 2:
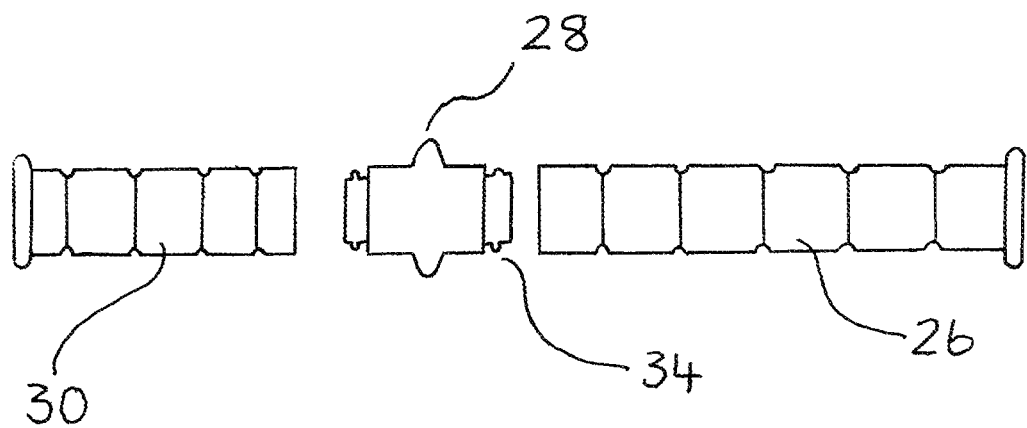
FIG. 2 is a perspective view of a handle member.

Referring to FIG. 2, the handle 12 includes a proximal portion 26, a distal portion 30, and a stop portion 28. The handle 12 may be monolithically formed and injection molded from a rigid polymer such as acrylonitrile butadiene styrene, polystyrene, polyetherketone, polyamide, polyethersulfone, polyurethane, ether block amide copolymers, polyacetal, and derivatives thereof. It is contemplated that the handle 12 can be integrally assembled of multiple sections and may be substantially transparent, opaque, etc. The handle 12 may also be variously configured and dimensioned such as, for example, rectangular, spherical, tapered etc.

The handle 12 can be joined by any appropriate process such as, for example, snap fit, adhesive, solvent weld, thermal weld, ultrasonic weld, screw, rivet, etc. In this configuration, the handle 12 is presented wherein the proximal portion 26, the distal portion 30, and the stop portion 28 are joined through a snap fit process. In one embodiment, the handle 12 is assembled by inserting the stop portion 28 into the proximal portion 26, and subsequently inserting the distal portion 30 into the stop portion 28. The stop portion 28 is disposed between the proximal portion 26 and the distal portion 30 to prevent axial movement of the proximal 14 and distal 16 handle members, as shown in FIG. 1, into one another.

The stop portion 28 takes the form of a circular ring with details 34 that are incorporated into the molding. The details 34 facilitate the insertion of the stop portion 28 into proximal portion 26 and the distal portion 30 of the handle 12. It is envisioned that the details 34 may create a permanent binding between the proximal portion 26, the stop portion 28, and the distal portion 30.

Figure 3:
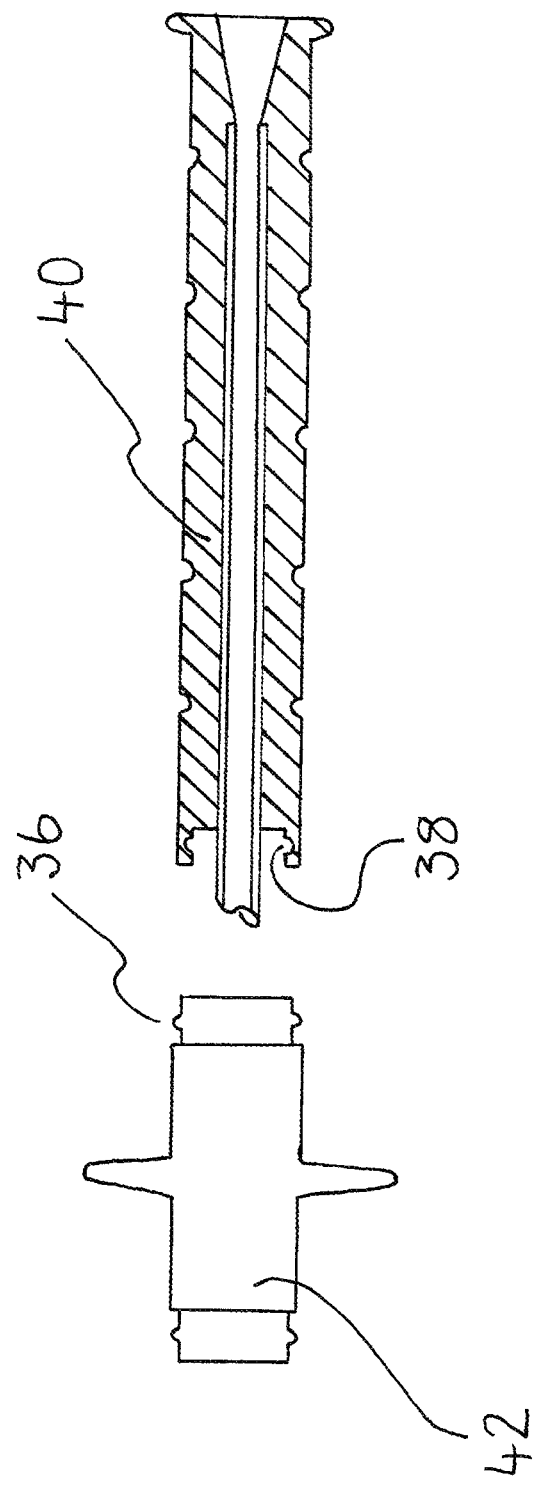
FIG. 3 is a cross-sectional view of a proximal portion of a handle member.

Referring to FIG. 3, an alternative embodiment is presented wherein the details 36 consist of a male and female mating configuration. The details 36 consists of a raised circular male ridge that fits into a female type depression 38 in the proximal portion of a handle 40. It is envisioned that an identical configuration can exist between the details 36 and the distal portion (not shown in Figure) of the handle 40. A configuration is further contemplated wherein a stop portion 42 includes details 36 that are female type depressions and the proximal and distal portions of the handle 40 includes a raised circular male ridge.

Figure 4:
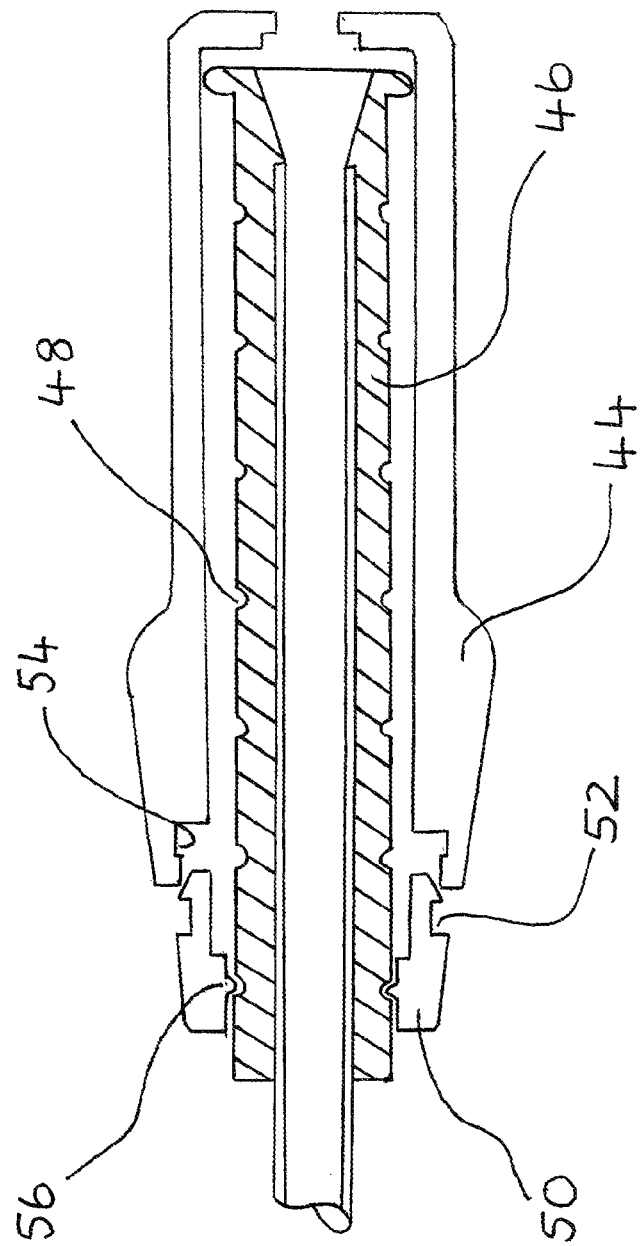
FIG. 4 is a cross-sectional view of a proximal portion of a handle member and a proximal handle member.

Turning to FIG. 4, a proximal portion of a handle 46 is presented wherein a proximal handle member 44 is disposed thereon. The handle 46 includes indentations 48 to facilitate slideable engagement along the axis of the handle 46. The indentations 48 may take the form of ribs, ridges, or other forms of detents. In a preferred embodiment, the indentations 48 are located at approximately one centimeter intervals along the handle 46.

In this configuration, the proximal handle member 44 incorporates a detail member 50. The detail member 50 provides a means for the proximal handle member 44 to engage the indentations 48. As previously presented in FIG. 3, the detail member 50 similarly include a male mating configuration to facilitate a snap fit engagement process. The detail member 50 includes a male ridge member 52, which fits into a female depression 54 and can form a permanent bond therebetween.

The detail member 50 includes friction members 56, which facilitate engagement with at least one indentation 48 of a first series of indentations 48 along the proximal portion of the handle 46. A frictional drag force is created between the friction members 56 engaging at least one indentation 48 of a first series of indentations 48. It is contemplated that the proximal handle member 44 and the detail member 50 may be joined via alternative processes such as adhesive, solvent weld, thermal weld, ultrasonic weld, etc.

The friction members 56 may be, but are not limited to, protrusions such as semi-circular barbs. In a preferred embodiment, the friction members 56 engage at least one indentation 48 of a first series of indentations 48 and provide a clinician with a definitive depth measurement of the proximal handle member 44. Additionally, the friction members 56 serves to securely lock the proximal handle member 44 in place to provide a clinician with a consistent point of reference. It is contemplated that multiple friction members 56 may be employed. It is further contemplated that friction members 56 may have flexible portions, which may be of varying flexibility according to the particular requirements of the handle 46.

Figure 5:
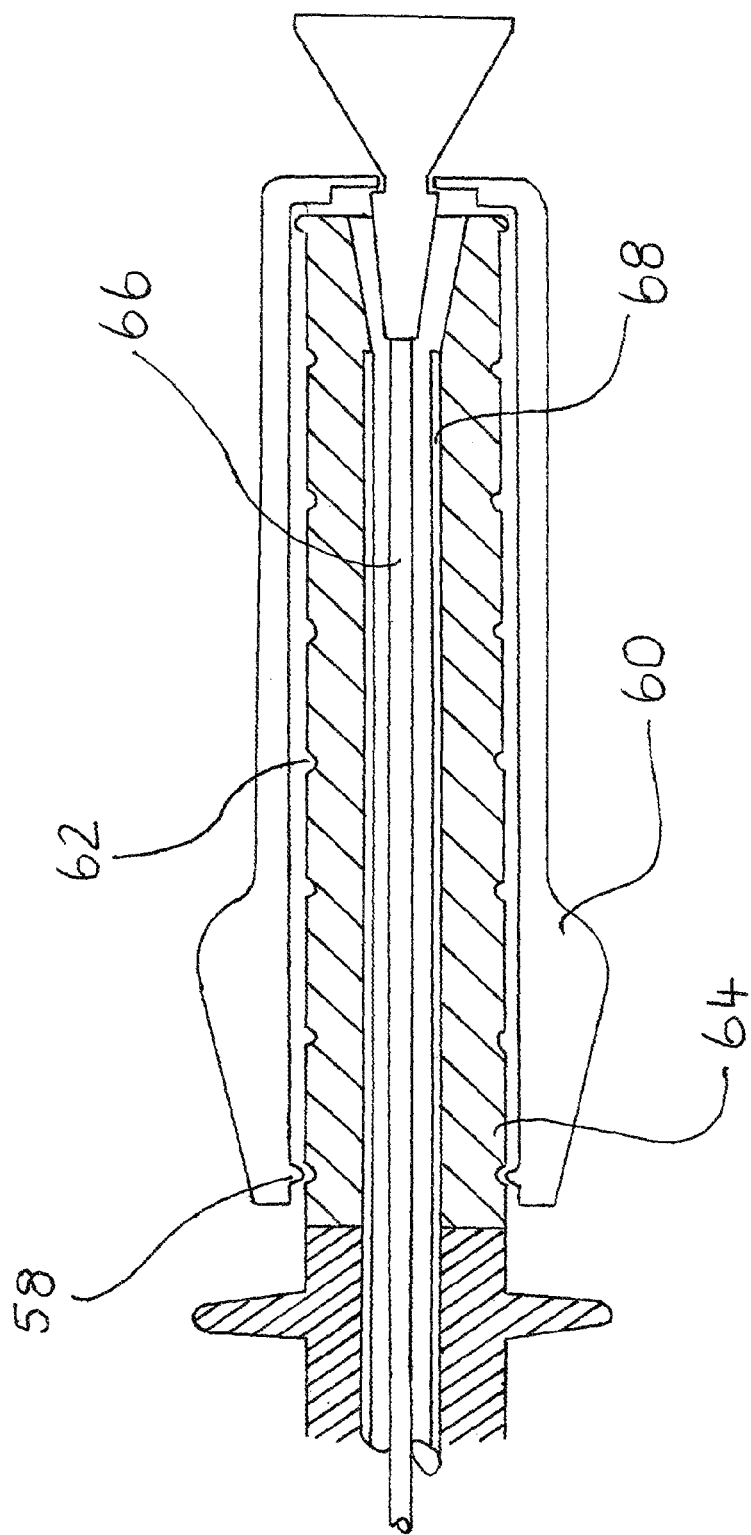
FIG. 5 is a cross-sectional view of an assembled proximal portion of a needle biopsy device.

Referring to FIG. 5, a proximal portion of a fully assembled handle 64 is presented wherein a proximal handle member 60 can slideably advance a needle 66 within a sheath 68. In this configuration, friction members 58 are disposed to a distal portion of the proximal handle member 60 as semi-circular barbs. As presented, the friction member 58 allow the proximal handle member 60 to engage indentations 62 at any of a plurality of positions along the axis of the handle member 64. It is contemplated that each of indentation 62 can represent a specific length by which the needle 66 extends relative to the sheath 68. More specifically, in an engaged position, a clinician can set a maximum length by which the needle 66 can extend beyond the distal end of the sheath 68. A clinician may easily manipulate the position of the needle 66 by applying pressure to the distal portion of the proximal handle member 60. It is envisioned that an excessive level of pressure is not required to move the proximal handle member. However, such pressure must be sufficient to overcome the frictional resistance created between the friction member 58 and at least one indentation 62.

Figure 6:
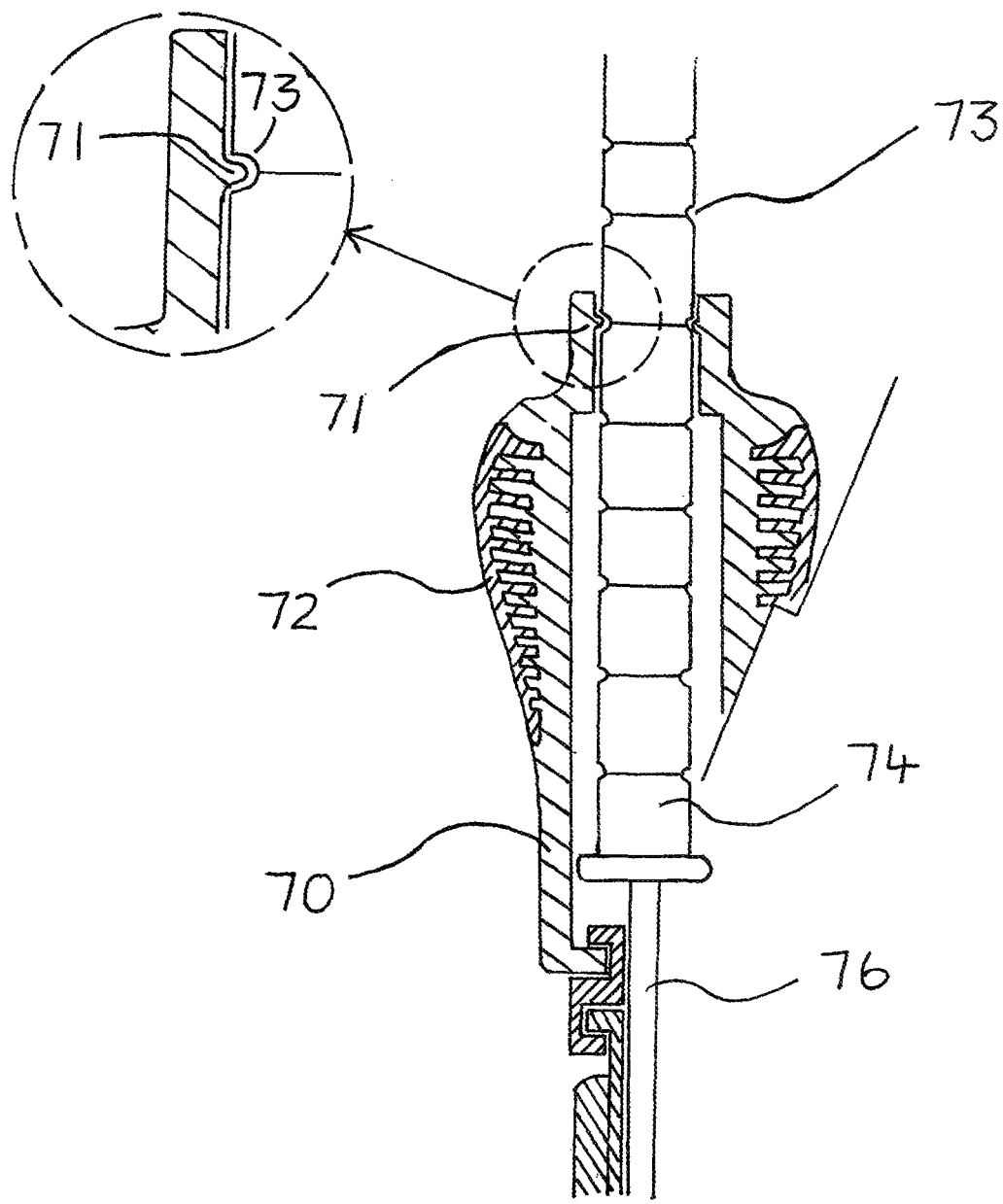
FIG. 6 is a partial cross-sectional view of an assembled distal portion of a needle biopsy device.
Figure 7:
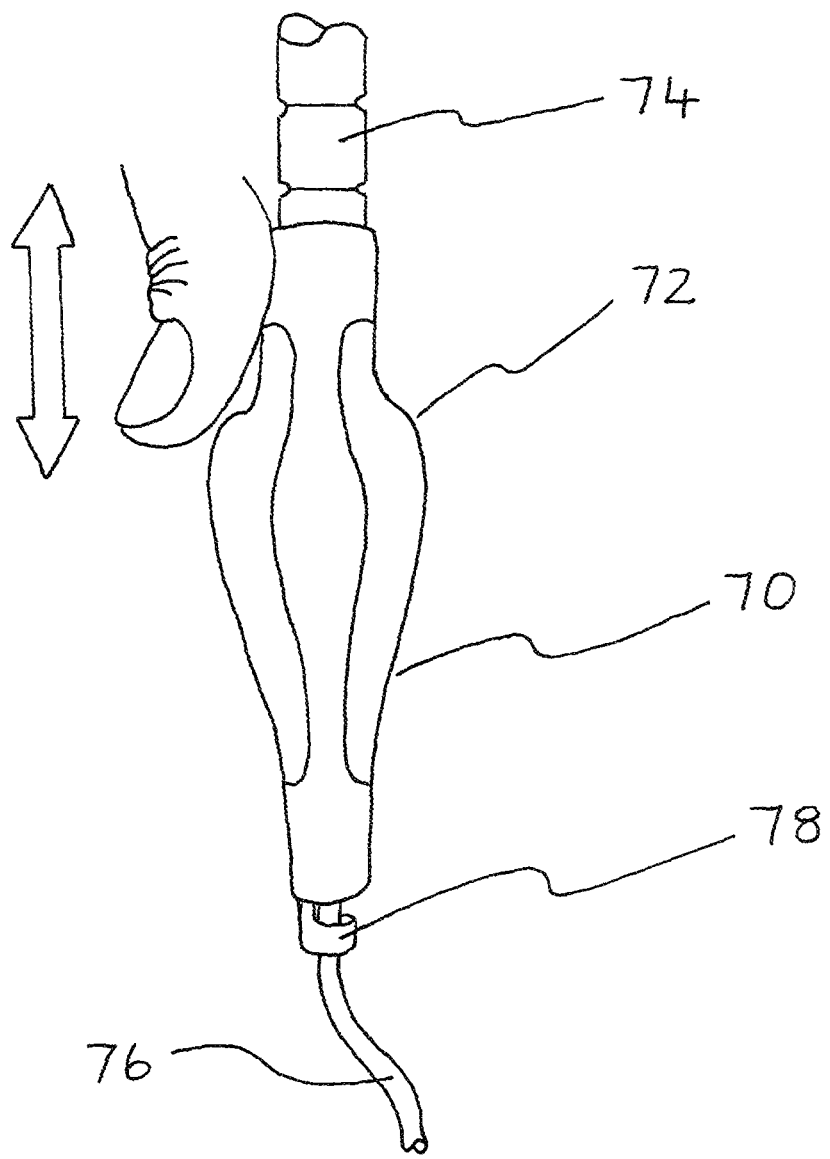
FIG. 7 is a perspective view of an assembled distal portion of a needle biopsy device.

Referring to FIGS. 6-7, a distal handle member 70 is presented that is identical to the proximal handle member as described in FIG. 5. The distal handle member 70 includes friction members 71, which facilitate engagement with at least one indentation 73 of a second series of indentations 73 along the distal portion of a handle 74. A frictional drag force is created between the friction members 71, which engage at least one indentation 73 of a second series of indentations 73 along the handle 74.

The proximal handle member (not shown in Figure) and the distal handle member 70 further include a structural adaptation 72 that facilitates seamless movement along the handle 74. In the present configuration, the structural adaptation 72 has a larger outer diameter than other portions of the distal handle member 70. Additionally, the structural adaptation 72 is ergonomically configured to serve as a resting position for a finger or thumb of a clinician. It is contemplated that the structural adaptation 72 may provide a surface that facilitates movement of the distal handle member 70 along the handle 74. It is envisioned that the surface may be comprised of materials such as a rubber or other polymeric materials. The structural adaptation 72 may also provide a clinician with a tactile feel measurement system for gauging the position of the sheath 76 relative to the handle 74.

The distal handle member 70 also provides a means for engaging the needle biopsy device to another medical device. Referring to FIG. 7, the distal handle member 70 provides a connector 78 to facilitate attachment of the device to another medical device. The connector 78 is structurally capable of interacting with a connector on another medical device such as a channel or luer port. This interaction between the connector 78 and a connector on another medical device (not shown in Figure) can be, but is not limited to, a mating or locking connection.

Figure 8:
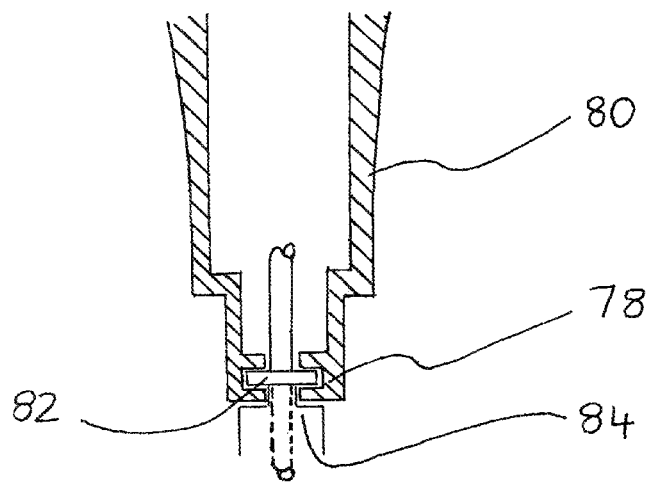
FIG. 8 is a cross-sectional view of a connector according to another embodiment of the invention.

Referring to FIG. 8, an alternative embodiment of a connector 78 is shown. The connector 78 provides a mechanism for the quick connect and disconnect of a needle biopsy device 80 from a channel port 82 of a medical device 84. The connector 78 includes an adaptation that provides for connection relative to the longitudinal axis of the medical device. It is contemplated that the adaptation may be a female mating configuration and may further provide for a side loading removal motion of the device 80 from the channel port 82. It is further contemplated that the connector 78 is sized such that the device 80 is securely locked onto the channel port 82 in both an axial and perpendicular direction.

Figure 9:
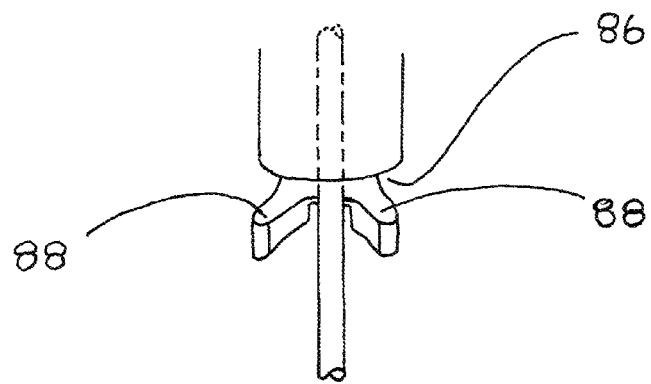
FIG. 9 is a perspective view of a connector according to another embodiment of the invention.

Referring to FIG. 9, another embodiment of a quick connect connector 86 is shown. The connector 86 includes two adaptations 88 that provide for connection relative to the longitudinal axis of the medical device. It is envisioned that the two adaptations 88 may represent a male mating configuration engaging a female mating channel port of another medical device. It is further envisioned that the two adaptations provide a secure connection to the medical device.

Figure 10:
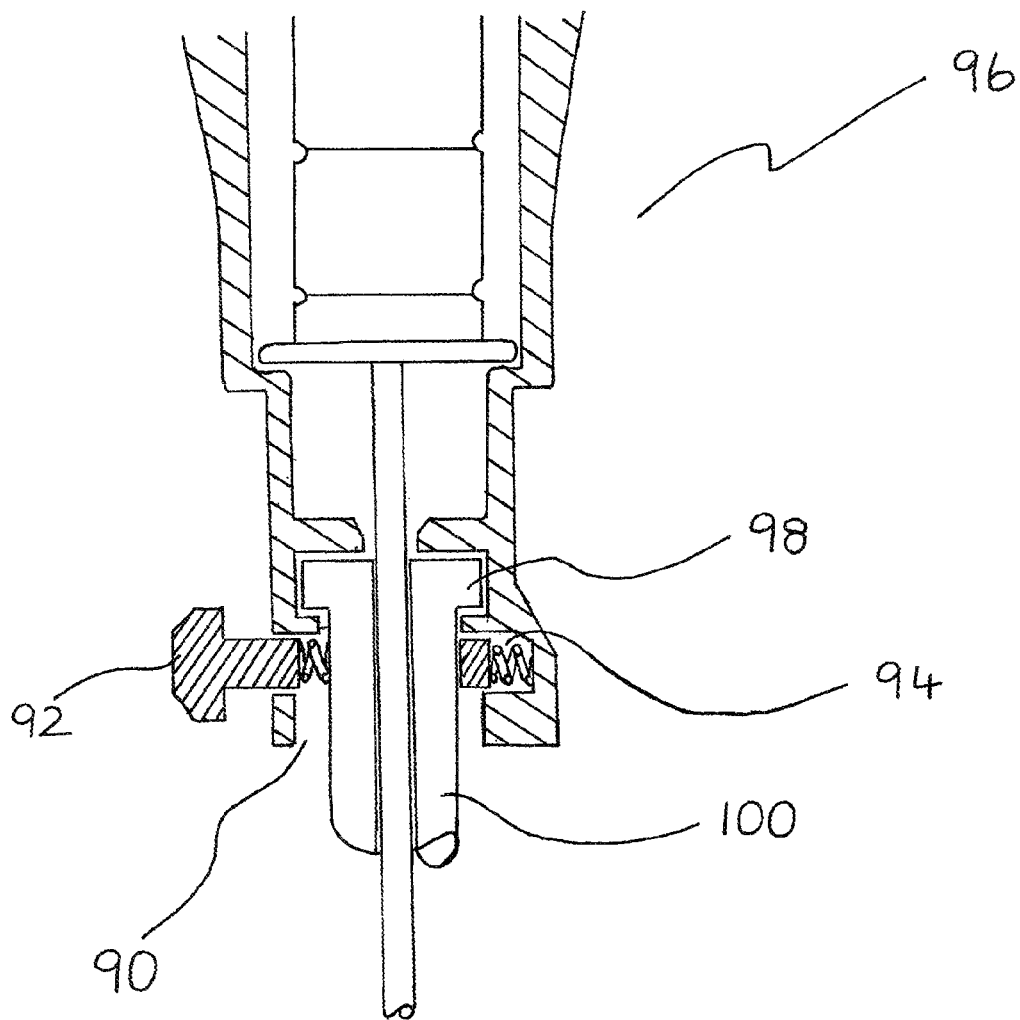
FIG. 10 is a cross-sectional view of a connector according to another embodiment of the invention.

Referring to FIG. 10, another embodiment of a connector 90 is shown. The connector 90 is a spring loaded mechanism which facilitates connection to other medical devices with different channel ports. In the present configuration, a clinician can quickly load a device 96 axially onto a channel port 98 of another medical device 100. A button 92 is provided to work in concert with a spring 94 to provide a spring loaded tension between the device 96 and another medical device 100. The button 92 may also be depressed to release the spring loading tension and disengage the device 96. It is contemplated that the button 92 may be situated in a position to allow the clinician to utilize their thumb or finger to depress the button 92 without disturbing the desired configuration of the device 96.

Figure 11:
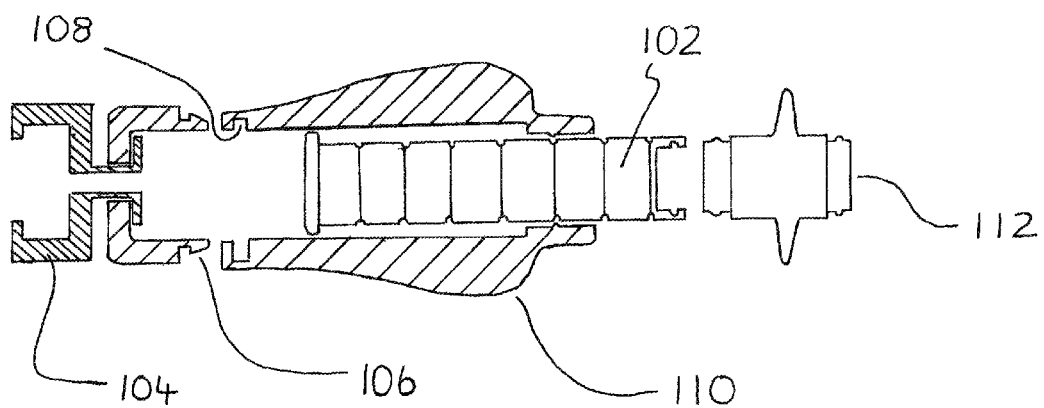
FIG. 11 is a partial cross-sectional view of a disassembled distal portion of the invention.

Referring to FIG. 11, a distal portion of a handle 102 is presented wherein a connector 104 is joined via a snap fit process. It is contemplated that the connector 104 may utilize a snap fit detail 106, which can be a male mating configuration that engages a female mating configuration 108. In one embodiment, the snap fit detail 106 is permanently locked to the female mating member 108. It is further contemplated that the connector 104 may be adaptations in the form of two protruding male mating adaptations, a female mating adaptation, a spring loading mechanism, etc to satisfy the need for a quick connection mechanism.

Referring to FIGS. 1, 4, and 11, the needle biopsy device may also be assembled by engaging the connector 104 to the distal handle member 110, and subsequently attaching the distal handle member 110 to a stop portion 112. The stop portion 112 may be attached to the handle 46, as shown in FIG. 4, to complete the assembly of the handle 12, as shown in FIG. 1.

Figure 13:
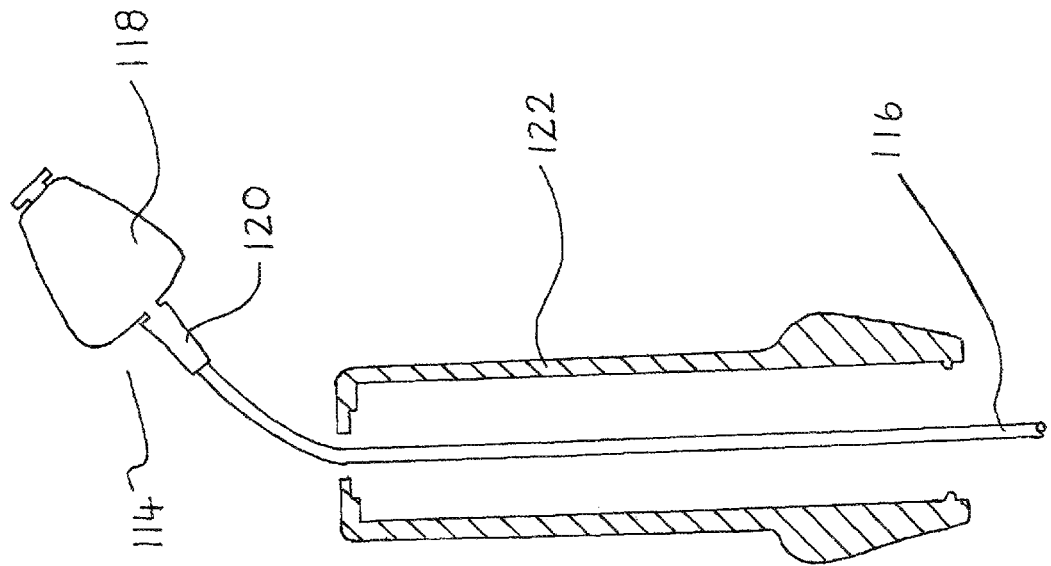
FIG. 13 is a perspective view of a needle housing member according to another embodiment of the invention.
Figure 12:
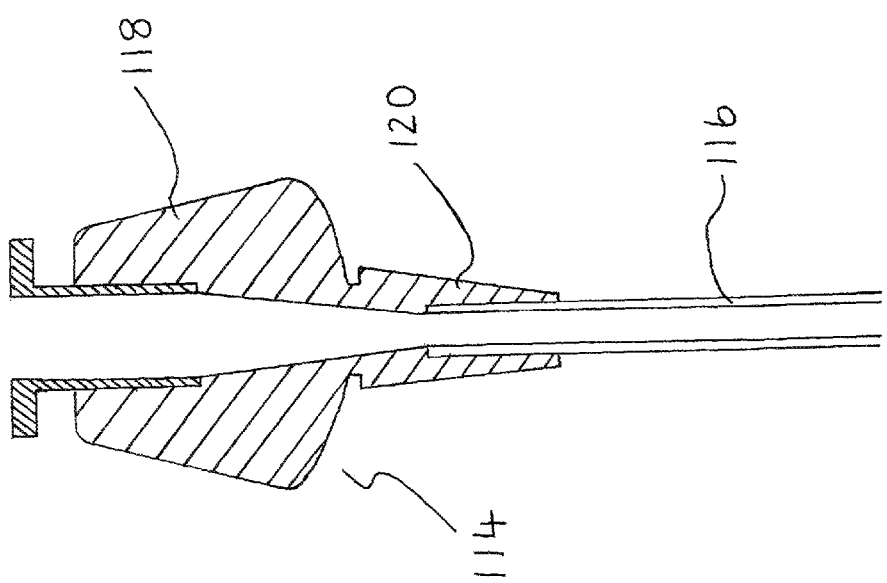
FIG. 12 is a perspective view of a needle housing member.

Turning to FIGS. 12 and 13, assembly of the needle biopsy device may be completed by inserting a needle housing member 114 into a proximal handle member 122. The needle housing member 114 is designed to allow a clinician to quickly and seamlessly remove the needle 116 after an aspirating sample is taken at a site of lesion or abnormality.

The needle housing member 114 includes a needle 116, a hub 118, and a strain relief 120. Due to the varying requirements of endoscopic ultrasound procedures, the needle 116 may be designed to range in length from fifty centimeters to two-hundred and fifty centimeters. Additionally, the needle 116 may be beveled via a single or double bevel at its distal end to aid a clinician in penetrating tissue in preparation of collecting an aspirated sample. It is contemplated that the needle 116 can be manufactured from several metallic based materials, such as stainless steel or alloys thereof and nitinol or alloys thereof. Alternatively, the needle 116 may be manufactured from polymeric materials including, but not limited to, polyetherketone, polyamide, polyethersulfone, polyurethane, ether block amide copolymers, polyacetal, polytetrafluoroethylene and derivatives thereof. Moreover, a combination of metallic based and polymeric materials may be suitable for this purpose. It is contemplated that one skilled in the art will realized that other materials suitable for manufacture in accordance with the present disclosure will also be appropriate.

The needle 116 requires a secure bond to the needle housing member 114. In one embodiment, the needle is attached to the needle housing member 114 via adhesive bonding. Although adhesive bonding is suitable for this purpose, an alternative and preferred method, such as direct injection over-molding can be utilized.

The method of over-molding consists of a two step molding operation with two constituent components. First, an inner component (not shown in the Figure) consists of a rigid polymer. The purpose of the inner component is to provide the primary bond between the hub 118 and the needle 116. It is contemplated that the inner component has shore hardness in the range of forty to eighty five Shore Durometer D. However, shore hardness in the range of seventy to eighty-five Shore Durometer D is generally preferable. It is contemplated that the shore hardness may include a scale of Shore Durometer A in addition to Shore Durometer D.

Second, the needle housing member 114 includes an outer component which consists of a strain relief 120. A common issue associated with prior art references is the kinking and deformation of needles during insertion and removal from a device. The strain relief 120 is designed to address the issue by providing a smooth transition and bend radius for the needle housing member 114 upon insertion and removal from the proximal handle member 112. The strain relief 120 is comprised of a relatively soft polymer, having shore hardness in the range of ten to fifty-five durometer. It is contemplated, however, that shore hardness in the range of thirty to forty-five durometer is preferable.

Figure 14:
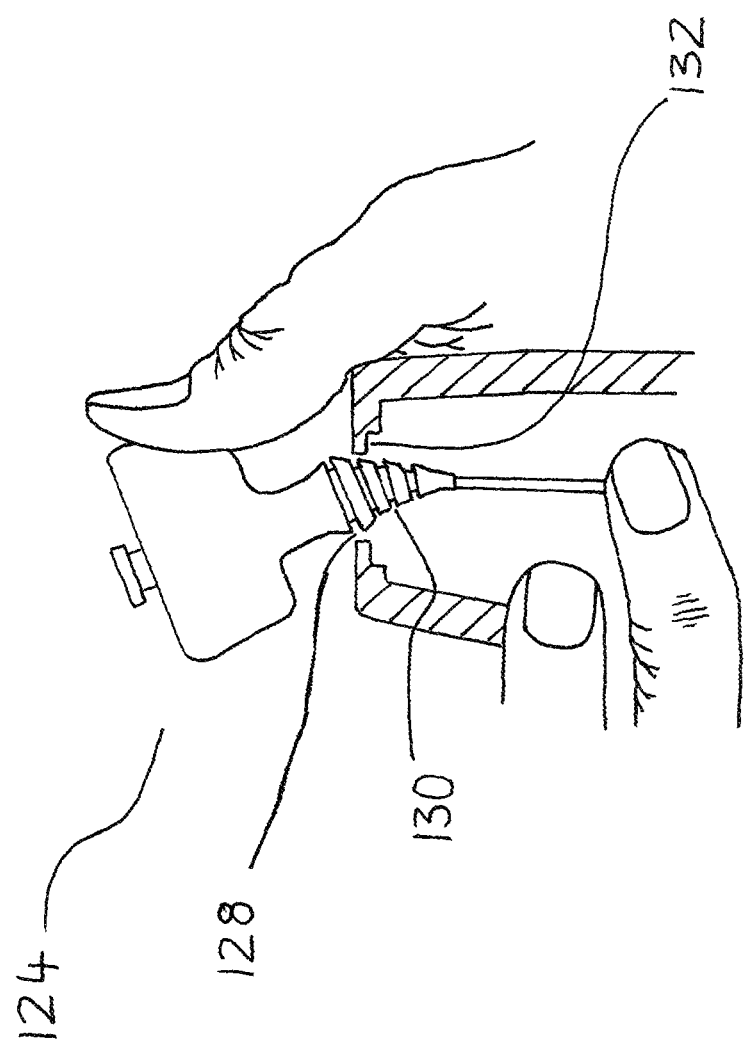
FIG. 14 is a perspective view of a needle housing member according to another embodiment of the invention.

Referring to FIG. 14, an alternative embodiment of the needle housing member 124 is shown. In the present configuration, the needle housing member 124 is loaded into an opening at the proximal portion of a proximal handle member 126. To limit the need for a clinician to remove their hand from the device, the needle housing member 124 provides connecting details 128 that are immediately proximal to a strain relief 130 to facilitate insertion and removal of the needle housing member 124. More specifically, the connecting details 128 provides a means for rapid connection and disengagement of the needle housing member 124 relative to the proximal handle member 126. Upon inserting the needle housing member 124 into the proximal handle member 126, female connecting details 130 engage male connecting details 132 housed on the proximal handle member 126. The engagement of the female connecting details 130 and the male connecting details 132 provides the needle housing member 124 with a secure lock in the axial direction. This lock ensures that the needle subassembly can not move or deform while is use.

The present configuration is designed to allow a clinician to easily disengage the needle housing member 124 from the proximal handle member 126. For example, once the clinician has acquired the desired tissue or fluid sample through needle aspiration, they may apply force in a substantially traverse direction to the needle housing member 124. The needle housing member 124 may be subsequently retracted for disposing the sample contained upon the needle. As a result, it is envisioned that a clinician can seamlessly acquire and insert another needle housing member 124 without reconfiguring the positions of the proximal handle member 126.

Figure 15:
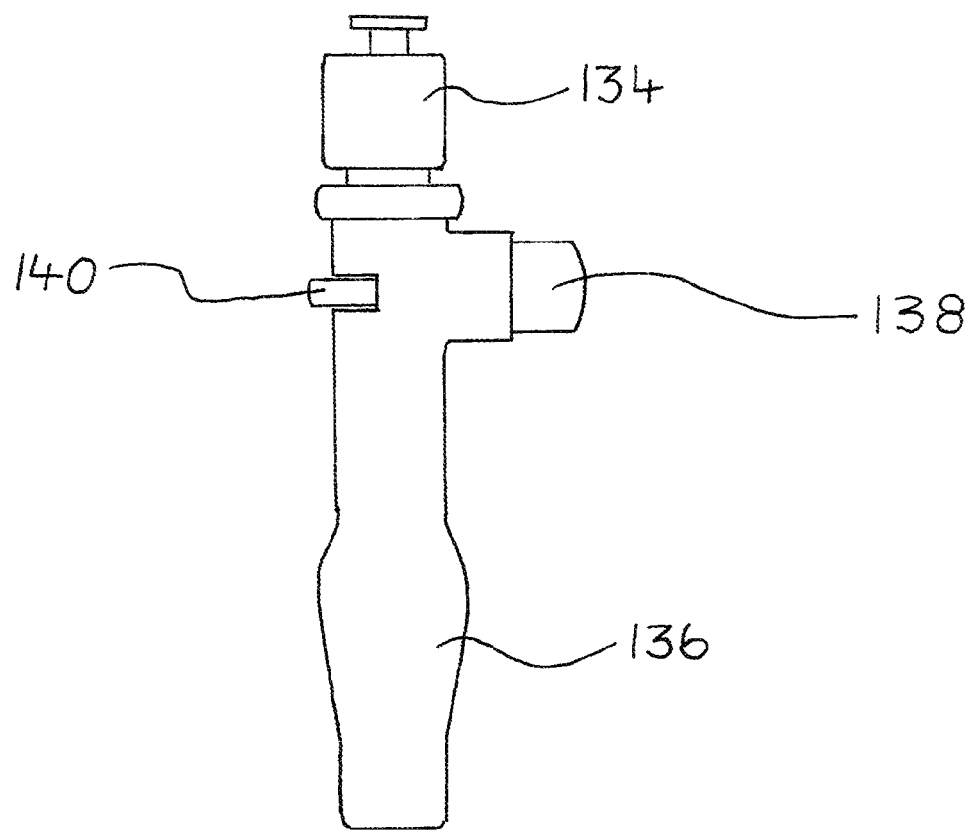
FIG. 15 is a perspective view of a needle housing member according to another embodiment of the invention.
Figure 16:
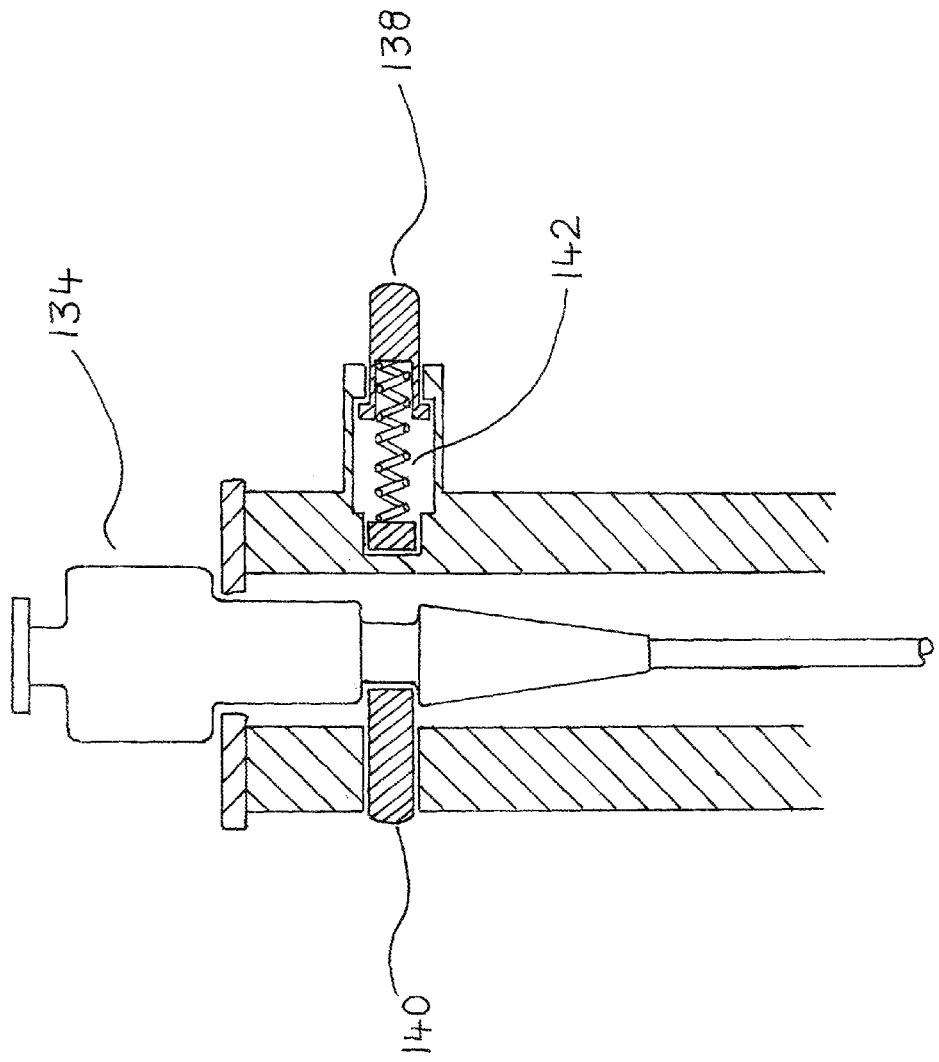
FIG. 16 is a cross-sectional view of a needle housing member according to another embodiment of the invention.

Referring to FIGS. 15 and 16, it is contemplated that a spring loaded mechanism may be provided to facilitate the removal of a needle housing member 134 from a device 136. In the present configuration, a release member 138 is provided which functions in concert with a lever 140. The lever 140 operates under a spring loaded tension 142 to securely fasten the needle housing member 134 to the device 136. The lever 140 is operated by depressing the release member 138. Upon depressing the release member 138, the tension released by a spring 142 causes the lever 140 to release the needle housing member 134 from the device 136.

Figure 17:
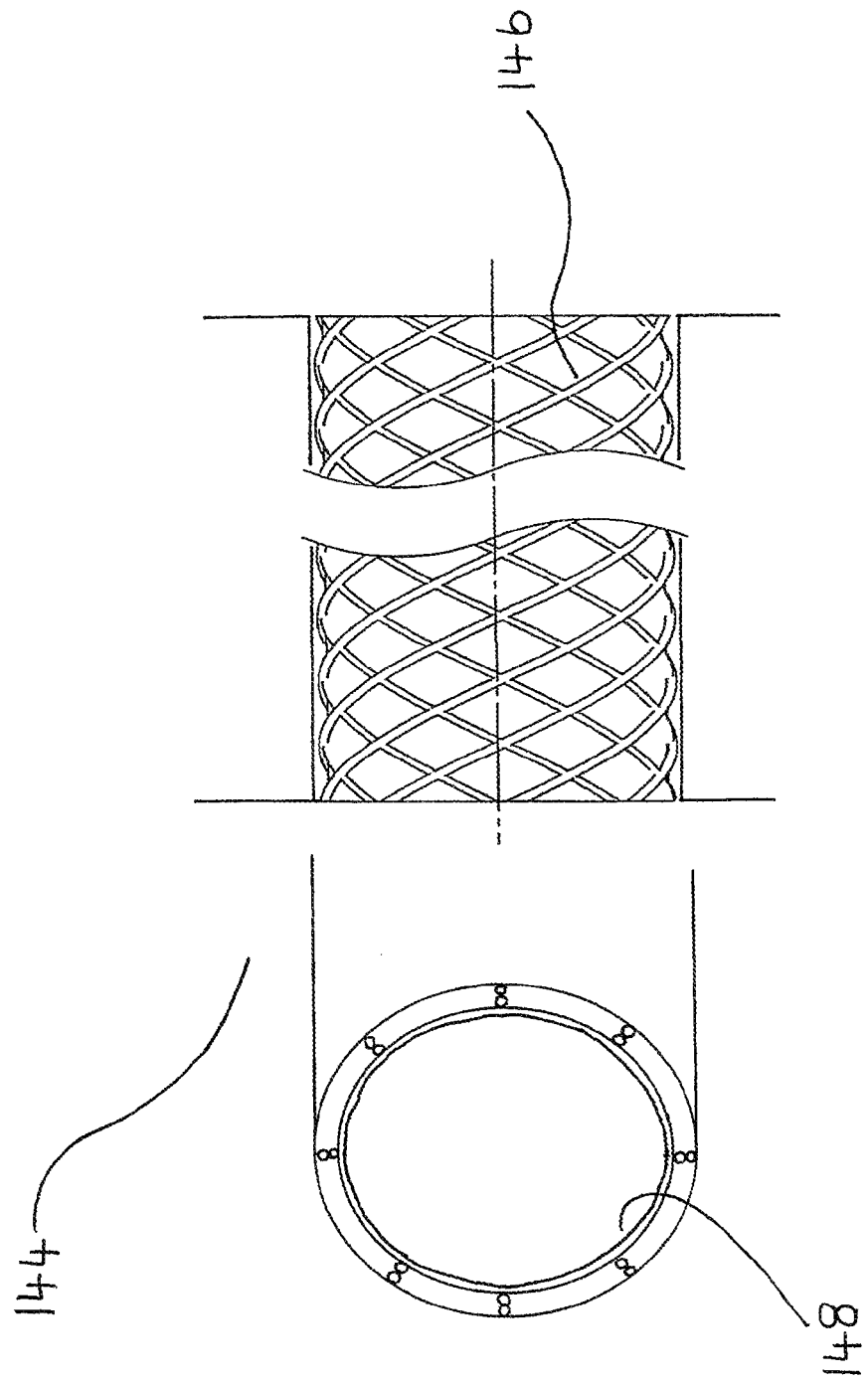
FIG. 17 is a perspective view of a sheath lumen.

Turning to FIG. 17, a sheath lumen 144 is provided to house the needle 22 from the proximal handle member 14 through the distal handle member 16, as shown in FIG. 1. The sheath lumen 144 is comprised of, but not limited to, thermoplastic materials. It is contemplated that the thermoplastic materials may be polyurethane, polyamide and derivatives thereof, ether block amide copolymers, polyimide, placental, polyethylene and derivates thereof, polytetrafluoroethylene, and the like. In a preferred embodiment, the sheath lumen 144 is comprised of a helically braided configuration 146 of outer thermoplastic materials with a lubricious inner core 148.

The inner core 148 may be made from polytetrafluoroethylene, fluorinated ethylene propylene, or derivatives thereof, to provide a lubricous surface for the needle 22, as shown in FIG. 1, as it is passed through the sheath lumen 144. It is contemplated that the sheath lumen 144 may have an outer diameter ranging from three French to twelve French. It is further contemplated that the sheath lumen 144 may have an inner diameter ranging from two French to ten French. In a preferred embodiment, the inner and outer diameter of the sheath 144 is between three French and six French.

Figure 18:
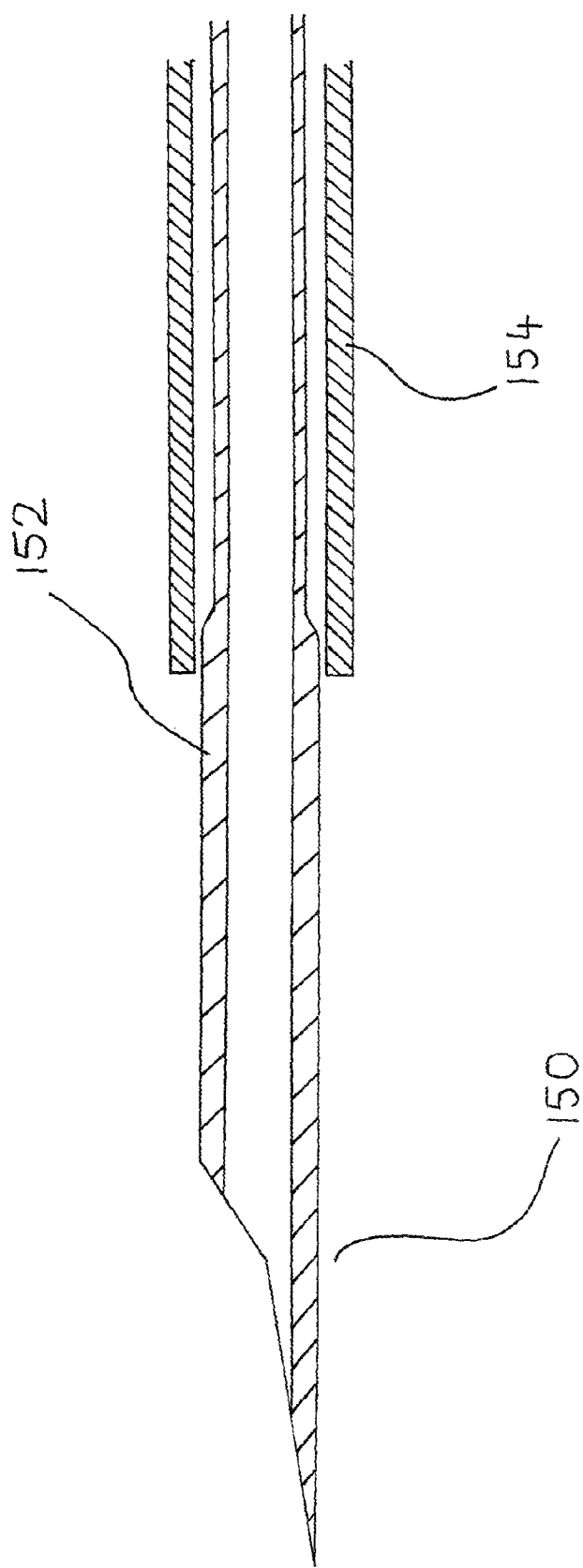
FIG. 18 is a cross-sectional view of a needle according to another embodiment of the invention.

Referring to FIG. 18, a taper 152 on the distal end of a needle 150 may be provided to provide a level of interference between a sheath 154 and the needle 150 during needle advancement. The taper 152 addresses the issue of needle instability by providing an enlarged portion that provides a frictional resistance in the form of a drag force. It is envisioned that the taper 152 may be incorporated onto the needle 150 through centerless grinding or cold-drawing techniques.

Figure 19:
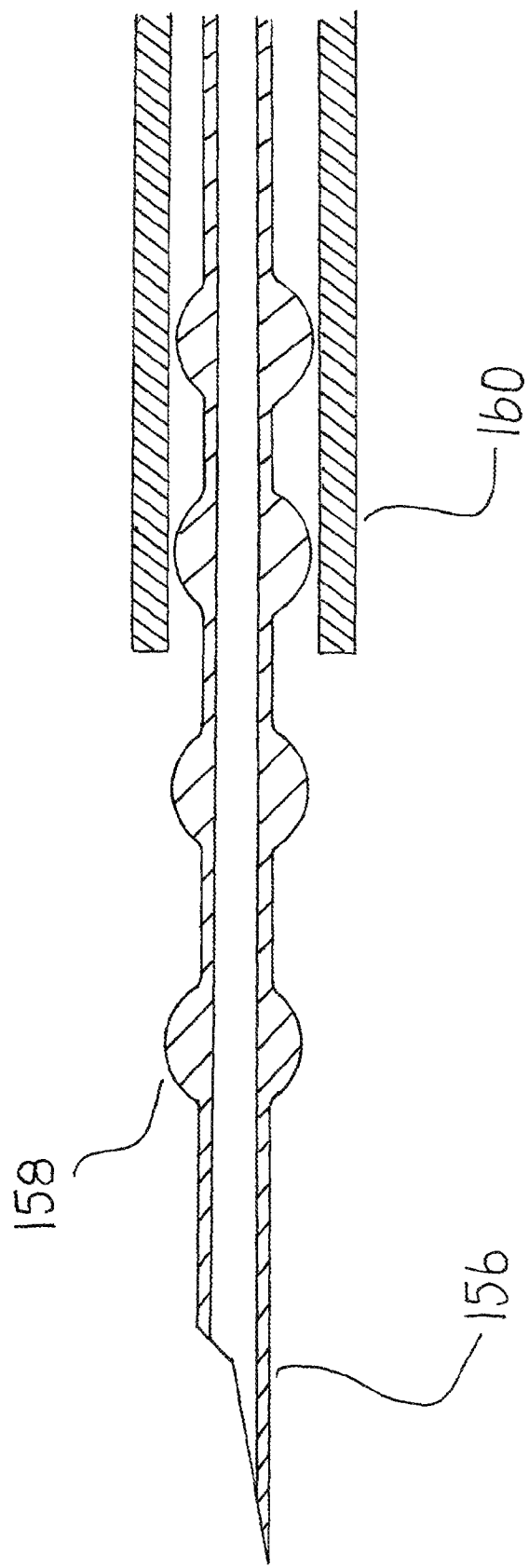
FIG. 19 is a cross-sectional view of a needle according to another embodiment of the invention.

Referring to FIG. 19, an alternative embodiment is presented wherein a needle 156 comprises stabilizing bulbs 158 located at constant increments over the length of the needle 156. These bulbs 158 may be spaced anywhere from two millimeters to one centimeter apart and may be located over the entire length of the needle 156 or over a portion of the needle 156. It is contemplated that the bulbs 158 may be circular or elliptical in geometry and may be incorporated onto the needle 156 via soldering or laser welding or incorporating into the grind profile of the needle 156. It is further contemplated that the stabilizing bulbs 158 will provide sufficient frictional resistance between the needle 156 and a sheath 160.

Figure 20:
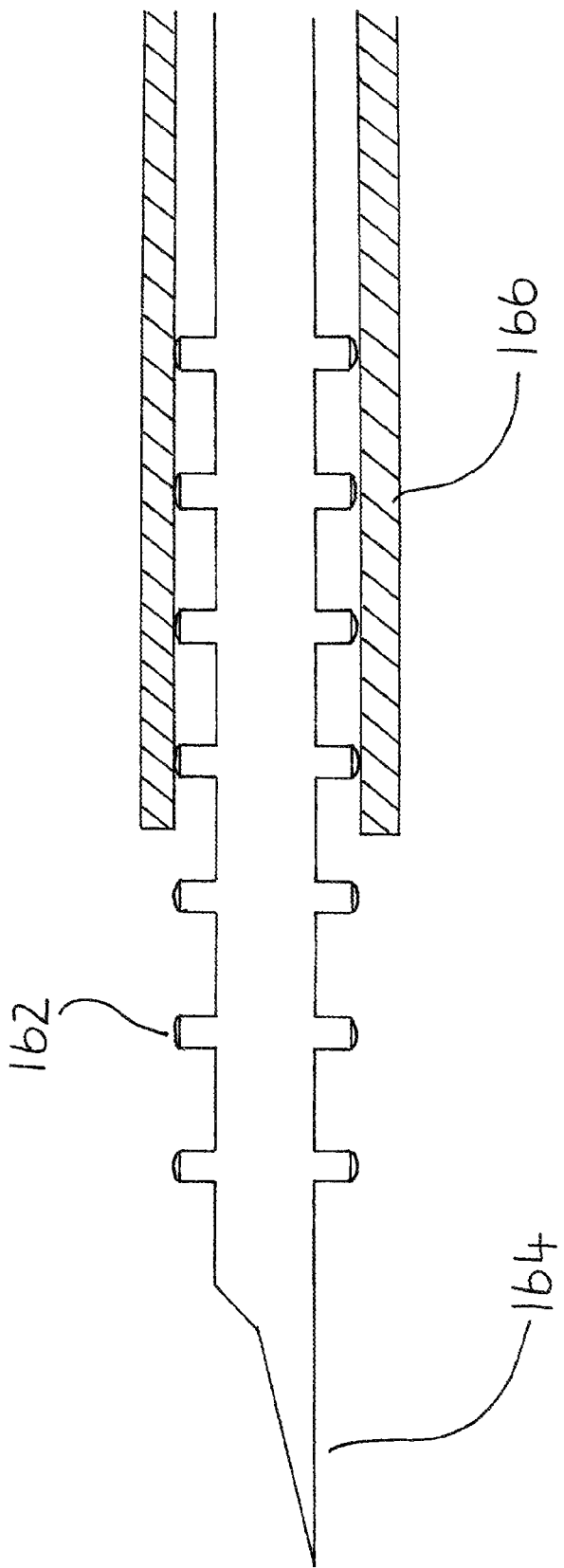
FIG. 20 is a cross-sectional view of a needle according to another embodiment of the invention.

Referring to FIG. 20, another embodiment is contemplated wherein a series of barbs 162 are located at varying intervals along the length of a needle 164. The purpose of the barbs 162 is to reduce the effective clearance between the outer diameter of the needle 164 and the inner diameter of a sheath 166. It is contemplated that the barbs 162 may be positioned at the distal end of the needle 164 or alternately, may be spaced over the entire length of the needle 164.

It is contemplated that all forms of protrusions, including the "taper", "bulb" or "barb" details, extend into the sheath 166 when the needle 164 is fully extended relative to the sheath 166. This ensures that at maximum needle insertion depth, the needle 164 is kept stable in the assembly and achieves the desired design intent.

Figure 21:
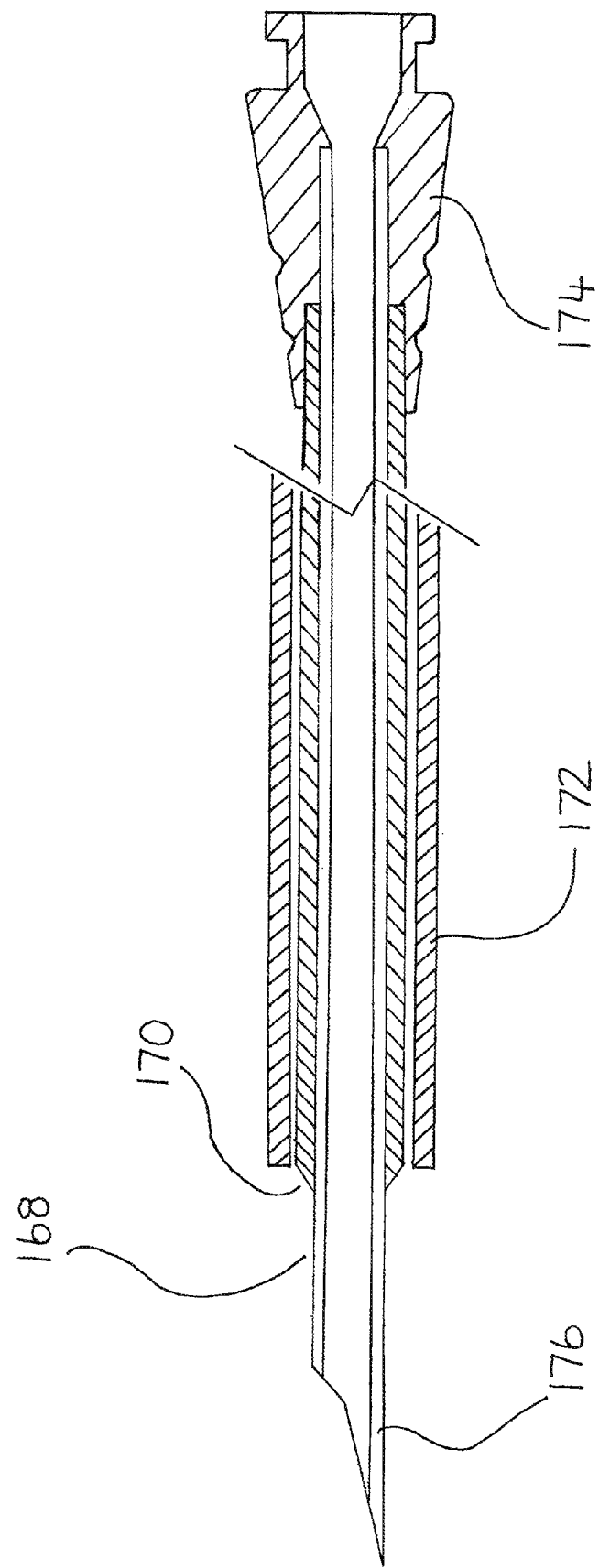
FIG. 21 is a cross-sectional view of a needle according to another embodiment of the invention.

Referring to FIG. 21, a clinician may yield the benefit of improving the echogenicity and ultrasonic visibility of a needle 168 during endoscopic ultrasound, by enhancing the definition of the needle 168 and the ability to discern needle 168 during the procedure. It is contemplated that the needle 168 can be surrounded by echogenic materials such as a polymer impregnated with sonically reflective particles to provide ultrasonic visibility. It is further contemplated that ultrasonic visibility may be, but is not limited to, x-rays, ultrasounds, sonography, etc. It is envisioned that the polymer may be, but is not limited to, a thermoplastic or thermoset coating. It is further contemplated that the echogenic properties of the needle 168 may be enhanced through techniques such as sandblasting, laser etching, surface roughening, the introduction of various patterned geometries onto the surface of the needle, etc.

In the present configuration, an alternative configured is contemplated wherein a polymeric sleeve or jacket 170 covers the proximal portion of the needle 160, which extends distally from a sheath 172 back to a hub on a housing member 174. The purpose of the sheath 172 is to act as a "buffer-layer" between the outer diameter of the needle 168 and the inner diameter of the sheath 172. In this way, the advancement of smaller diameter needles are stabilized as a result of frictional resistance between the needle 168 and the sheath 172. The material used for the needle jacket 170 is preferably extruded from a thermoplastic material such as polyurethane, polyethylene, polypropylene or copolymers thereof, polyamide, polyimide, and polyether block amide or copolymers thereof. Alternately and more preferably, the jacket 170 may be extruded from a highly lubricious material such as polytetrafluoroethylene or fluorinated ethylene-propylene. It is contemplated that by utilizing low co-efficient of friction materials on the outer wall of the needle 168, the frictional drag or insertion force required to insert the needle 168 through the sheath 172 to the desired anatomical location for aspiration is minimized.

In the present configuration, the polymeric jacket or sleeve 170 is located to commence at the needle housing member 174 and run the entire length of the needle 168 to a specified location. This method ensures that the distal portion of the needle 168, which extends from the sheath 172, is bare and the polymeric jacket 170 does not interfere with passage of the needle 168 through the clinical anatomical mass under evaluation. The jacket 170 may be captured at the proximal end during insert molding of the needle housing member 174 or alternately may abut the needle housing member 174.

The incorporation of such a polymeric jacket 170 to encase the proximal portion of the needle 168 also serves to provide the clinician with passive feedback during removal of the needle 168 from the proximal handle housing. During removal of the needle 168 from the device once the sample has been acquired, it is important that the clinician be made aware of when they are approaching the sharp end of the needle 168. With the polymeric jacket 170 being positioned at a constant distance from the sharp bevel of the needle 168, once the clinician observes the end of the polymeric jacket 170 on the needle 168, they are passively made aware that a sharp bevel 176 is located at a specified distance from the end of the polymeric jacket 170. This passive feedback is important as the clinician can now exercise additional caution to ensure that they do not inadvertently pierce themselves with the needle 168 or cause the needle 168 to become entangled, endangering the diagnosing value of the collected sample.

It is contemplated that these concepts pertain to the maintenance of stability during needle advancement, particularly in the case of a needle 168 with 22 or 25 AWG, wherein the gap between outer diameter of the needle 168 and inner diameter of the sheath 172 is more appreciable. It is desirable to also incorporate the jacket type arrangement into the design for the 19 AWG needle portion. With a reduced amount of concentric clearance available between inner diameter of the sheath 172 and the outer diameter of the needle 168 in the case of a 19 AWG needle 168, the polymer jacket 170 may take the form of polytetrafluoroethylene or other thermoplastic material heat shrink which is thermally laminated onto the outer diameter of the needle 168. Alternately, it is further contemplated that a 19 AWG needle 168 may be spray coated with a lubricious material such as teflon. At the distal end of the needle 168, the heat shrink material or coated material may terminate at specific distance from the sharp end of the needle 168. It is envisioned that this method will provide the clinician with feedback as to when they are approaching the sharp bevel at the distal end during extraction of the needle 168.

It will be understood that various modifications may be made to the embodiments disclosed herein. Therefore, the above description should not be construed as limiting, but merely as exemplifications of the various embodiments of the invention. Those skilled in the art will envision other modifications within the scope and spirit of the claims appended hereto.

What is claimed is:

1. A device for needle biopsy, comprising:
   a handle member having proximal and distal portions;
   a proximal handle member disposed at the proximal portion of the handle member the proximal handle member being configured for slideable engagement with the proximal portion of the handle member, the proximal handle member includes a friction member that engages at least one indentation of a first series of indentations along the proximal portion of the handle member to limit slideable movement of the proximal handle member relative to the proximal portion of the handle member;
   a distal handle member disposed at the distal portion of the handle member and configured to mate with another medical device including a channel, the distal handle member being configured for slideable engagement with the distal portion of the handle member, the distal handle member includes a friction member that engages at least one indentation of a second series of indentations along the distal portion of the handle member to limit slideable movement of the distal handle member relative to the distal portion of the handle member;
   a sheath, having a lumen, the sheath being disposed within the handle member and extending from the distal portion of the handle member;
   an exchangeable needle housing member, coupled to a flexible needle disposed within the sheath, the exchangeable needle housing member being releasably coupled to the proximal portion of the handle member and adapted to allow the needle housing member and needle to be removed from the device and exchanged with a different needle housing member and a different needle while the sheath remains disposed in the channel of the another medical device to which the distal handle member is mated, wherein the needle includes a plurality of protrusions disposed thereon, the protrusions centering the needle in the lumen of the sheath as the needle moves axially within the lumen, and at least a portion of the needle is surrounded by a polymer.

2. The device of claim 1, wherein the plurality of protrusions are distributed along the length of the needle.

3. The device of claim 1, wherein the plurality of protrusions are located at a consistent increment over the length of the needle.

4. The device of claim 1, wherein at least a portion of the needle includes a tapered region for increasing the overall dimension of the needle, wherein the tapered region and the sheath lumen provide an interference therebetween for creating stability for the needle as the needle passes through the sheath lumen and is removed from the sheath lumen.

5. The device of claim 4, wherein the interference is a drag force creating frictional resistance between an outer diameter of the needle and an inner diameter of the sheath lumen.

6. The device of claim 1, wherein at least a portion of the needle includes materials or design features to enhance echogenicity and ultrasonic visibility.

7. The device of claim 1, wherein the flexible needle additionally includes a stylet disposed therein.

8. The device of claim 1, wherein the polymer is comprised of lubricous materials.

9. The device of claim 1, wherein the polymer increases the overall dimension of the needle to create stability for the needle as the needle passes through the sheath lumen and is removed from the sheath lumen.

* * * * *